US012758251B2

(12) United States Patent
Romoda

(10) Patent No.: US 12,758,251 B2
(45) Date of Patent: Oct. 13, 2026

(54) BI-MODAL INTRAOCULAR SHUNT INSERTER

(71) Applicant: Aquesys, Inc., North Chicago, IL (US)

(72) Inventor: Laszlo O. Romoda, San Clemente, CA (US)

(73) Assignee: Aquesys, Inc., North Chicago, IL (US)

( * ) Notice: Subject to any disclaimer, the term of this patent is extended or adjusted under 35 U.S.C. 154(b) by 945 days.

(21) Appl. No.: 17/799,720

(22) PCT Filed: Feb. 19, 2021

(86) PCT No.: PCT/US2021/018922
§ 371 (c)(1),
(2) Date: Aug. 15, 2022

(87) PCT Pub. No.: WO2021/168364
PCT Pub. Date: Aug. 26, 2021

(65) Prior Publication Data

US 2023/0062291 A1 Mar. 2, 2023

Related U.S. Application Data

(60) Provisional application No. 62/979,353, filed on Feb. 20, 2020.

(51) Int. Cl.

| | |
|---|---|
| ***A61B 17/34*** | (2006.01) |
| ***A61B 17/00*** | (2006.01) |
| ***A61F 9/007*** | (2006.01) |

(52) U.S. Cl.
CPC .......... *A61B 17/34* (2013.01); *A61F 9/00781* (2013.01); *A61B 2017/00367* (2013.01)

(58) Field of Classification Search
CPC .......... A61B 17/34; A61B 2017/00367; A61B 17/3468; A61B 2017/0038;
(Continued)

(56) References Cited

U.S. PATENT DOCUMENTS

| | | | |
|---|---|---|---|
| 2,902,995 | A | 9/1959 | Loper |
| 3,491,757 | A | 1/1970 | Arce |

(Continued)

FOREIGN PATENT DOCUMENTS

| | | | |
|---|---|---|---|
| CA | 2704695 | A1 | 5/2008 |
| CN | 1402625 | A | 3/2003 |

(Continued)

OTHER PUBLICATIONS

Quere, D.; "Fluid Coating on a Fiber," Annu, Rev. Fluid Mech, 1999, 31: pp. 347-384 (38 pgs).

(Continued)

*Primary Examiner* — Philip R Wiest
*Assistant Examiner* — Quynh Dao Le
(74) *Attorney, Agent, or Firm* — Stanek Lemon Crouse & Meeks, PA

(57) ABSTRACT

An inserter can include a needle, an actuation member, a plunger and/or assembly. The needle can define a lumen, and the plunger assembly can include a plunger and a plunger driver. The plunger can be at least partially disposed within the lumen of the needle, wherein the plunger is configured to advance a shunt through the lumen of the needle upon release. The plunger driver can be coupled to a proximal end portion of the plunger. The plunger driver elongates from a first length to a second length upon movement of the actuation member for advancing a distal end portion of the plunger from a first position to a second position relative to the lumen.

15 Claims, 12 Drawing Sheets

(58) Field of Classification Search
CPC ........... A61B 2017/347; A61F 9/00781; A61F 9/007; A61F 9/0017; A61F 9/0008; A61F 9/0026; A61F 2009/00891; A61F 2/95; A61F 2/167; A61F 2/1667; A61M 27/002; A61M 2210/0612; A61M 5/32; A61M 5/321; A61M 5/322
See application file for complete search history.

(56) References Cited

U.S. PATENT DOCUMENTS 3,654,932 A 4/1972 Newkirk et al.
3,788,327 A 1/1974 Donowitz
3,960,150 A 6/1976 Hussain et al.
4,013,080 A 3/1977 Froning
4,090,530 A 5/1978 Lange
4,402,308 A 9/1983 Scott
4,431,688 A 2/1984 Kornmann
4,562,463 A 12/1985 Lipton
4,583,117 A 4/1986 Lipton et al.
4,613,329 A 9/1986 Bodicky
4,700,692 A 10/1987 Baumgartner
4,722,724 A 2/1988 Schocket
4,730,613 A 3/1988 Gordy
4,740,205 A 4/1988 Seltzer et al.
4,744,362 A 5/1988 Grundler
4,750,901 A 6/1988 Molteno
4,787,885 A 11/1988 Binder
4,804,382 A 2/1989 Turina et al.
4,820,626 A 4/1989 Williams et al.
4,826,478 A 5/1989 Schocket
4,836,201 A 6/1989 Patton et al.
4,848,340 A 7/1989 Bille et al.
4,863,457 A 9/1989 Lee
4,902,292 A 2/1990 Joseph
4,908,024 A 3/1990 Py
4,911,161 A 3/1990 Schechter
4,915,684 A 4/1990 MacKeen et al.
4,934,363 A 6/1990 Smith et al.
4,936,825 A 6/1990 Ungerleider
4,946,436 A 8/1990 Smith
4,948,436 A 8/1990 Juergens
4,968,296 A 11/1990 Ritch et al.
4,976,688 A 12/1990 Rosenblum
4,978,352 A 12/1990 Fedorov et al.
4,997,419 A 3/1991 Lakatos et al.
5,035,695 A 7/1991 Weber, Jr. et al.
5,041,081 A 8/1991 Odrich
5,057,098 A 10/1991 Zelman
5,071,408 A 12/1991 Ahmed
5,092,837 A 3/1992 Ritch et al.
5,098,426 A 3/1992 Sklar et al.
5,098,443 A 3/1992 Parel et al.
5,162,641 A 11/1992 Fountain
5,167,645 A 12/1992 Castillo
5,178,604 A 1/1993 Baerveldt et al.
5,180,362 A 1/1993 Worst
5,201,750 A 4/1993 Hocherl et al.
5,207,660 A 5/1993 Lincoff
5,250,054 A 10/1993 Li
5,273,530 A 12/1993 Del Cerro et al.
5,275,622 A 1/1994 Lazarus et al.
5,290,295 A 3/1994 Querals et al.
5,300,020 A 4/1994 L'Esperance, Jr.
5,333,619 A 8/1994 Burgio
5,338,291 A 8/1994 Speckman et al.
5,342,370 A 8/1994 Simon et al.
5,351,678 A 10/1994 Clayton et al.
5,360,339 A 11/1994 Rosenberg
5,368,015 A 11/1994 Wilk
5,370,607 A 12/1994 Memmen
5,372,583 A 12/1994 Roberts et al.
5,399,951 A 3/1995 Lavallee et al.
5,410,638 A 4/1995 Colgate et al.
5,441,483 A 8/1995 Avitall
5,443,505 A 8/1995 Wong et al.
5,472,439 A 12/1995 Hurd
5,476,445 A 12/1995 Baerveldt et al.
5,516,522 A 5/1996 Peyman et al.
5,520,631 A 5/1996 Nordquist et al.
5,545,206 A 8/1996 Carson
5,558,629 A 9/1996 Baerveldt et al.
5,558,630 A 9/1996 Fisher
5,601,094 A 2/1997 Reiss
5,651,782 A 7/1997 Simon et al.
5,656,026 A 8/1997 Joseph
5,665,093 A 9/1997 Atkins et al.
5,665,114 A 9/1997 Weadock et al.
5,670,161 A 9/1997 Healy et al.
5,688,562 A 11/1997 Hsiung
5,695,474 A 12/1997 Daugherty
5,702,414 A 12/1997 Richter et al.
5,704,907 A 1/1998 Nordquist et al.
5,707,376 A 1/1998 Kavteladze et al.
5,709,668 A * 1/1998 Wacks ................ A61M 5/2033 222/326
5,722,948 A 3/1998 Gross
5,743,868 A 4/1998 Brown et al.
5,763,491 A 6/1998 Brandt et al.
5,824,072 A 10/1998 Wong
5,868,697 A 2/1999 Richter et al.
5,868,771 A 2/1999 Herbert et al.
5,888,200 A 3/1999 Walen
5,908,449 A 6/1999 Bruchman et al.
5,928,424 A 7/1999 Krebs et al.
5,932,299 A 8/1999 Katoot
5,938,583 A 8/1999 Grimm
5,964,747 A 10/1999 Eaton et al.
5,968,058 A 10/1999 Richter et al.
6,007,511 A 12/1999 Prywes
6,007,578 A 12/1999 Schachar
6,050,970 A 4/2000 Baerveldt
6,086,543 A 7/2000 Anderson et al.
6,102,045 A 8/2000 Nordquist et al.
6,146,366 A 11/2000 Schachar
6,159,218 A 12/2000 Aramant et al.
6,165,210 A 12/2000 Lau et al.
6,203,513 B1 3/2001 Yaron et al.
6,221,029 B1 4/2001 Mathis et al.
6,228,023 B1 5/2001 Zaslavsky et al.
6,228,873 B1 5/2001 Brandt et al.
6,231,546 B1 5/2001 Milo et al.
6,261,256 B1 7/2001 Ahmed
6,264,665 B1 7/2001 Yu et al.
6,280,468 B1 8/2001 Schachar
6,309,374 B1 10/2001 Hecker et al.
6,413,540 B1 7/2002 Yaacobi
6,450,937 B1 9/2002 Mercereau et al.
6,450,984 B1 9/2002 Lynch et al.
6,464,698 B1 10/2002 Falwell
6,464,724 B1 10/2002 Lynch et al.
6,468,283 B1 10/2002 Richter et al.
6,471,666 B1 10/2002 Odrich
6,483,930 B1 11/2002 Musgrave et al.
6,510,600 B2 1/2003 Yaron et al.
6,514,238 B1 2/2003 Hughes
6,524,275 B1 2/2003 Lynch et al.
6,533,768 B1 3/2003 Hill
6,544,249 B1 4/2003 Yu
6,558,342 B1 5/2003 Yaron et al.
6,595,945 B2 7/2003 Brown
6,626,858 B2 9/2003 Lynch et al.
6,638,239 B1 10/2003 Bergheim et al.
6,645,183 B2 11/2003 Christensen et al.
6,666,841 B2 12/2003 Gharib et al.
6,676,998 B2 1/2004 Huang et al.
6,699,210 B2 3/2004 Williams et al.
6,726,664 B2 4/2004 Yaron et al.
D490,152 S 5/2004 Myall et al.
6,730,056 B1 5/2004 Ghaem et al.
6,736,791 B1 5/2004 Tu et al.
6,752,753 B1 6/2004 Hoskins et al.
6,780,164 B2 8/2004 Bergheim et al.
6,783,544 B2 8/2004 Lynch et al.
6,827,699 B2 12/2004 Lynch et al.

(56) References Cited

U.S. PATENT DOCUMENTS 6,827,700 B2 12/2004 Lynch et al.
6,881,198 B2 4/2005 Brown
6,899,717 B2 5/2005 Weber et al.
6,936,053 B1 8/2005 Weiss
6,939,298 B2 9/2005 Brown et al.
6,955,656 B2 10/2005 Bergheim et al.
6,962,177 B1 11/2005 McCommons
6,981,958 B1 1/2006 Gharib et al.
7,008,396 B1 3/2006 Straub
7,037,335 B2 5/2006 Freeman et al.
7,041,077 B2 5/2006 Shields
7,094,225 B2 8/2006 Tu et al.
7,118,547 B2 10/2006 Dahan
7,135,009 B2 11/2006 Tu et al.
7,163,543 B2 1/2007 Smedley et al.
7,186,232 B1 3/2007 Smedley et al.
7,192,412 B1 3/2007 Zhou et al.
7,207,980 B2 4/2007 Christian et al.
7,220,238 B2 5/2007 Lynch et al.
7,273,475 B2 9/2007 Tu et al.
7,291,125 B2 11/2007 Coroneo
7,297,130 B2 11/2007 Bergheim et al.
7,297,154 B2 11/2007 Tu et al.
7,331,984 B2 2/2008 Tu et al.
7,344,528 B1 3/2008 Tu et al.
7,431,709 B2 10/2008 Pinchuk et al.
7,431,710 B2 10/2008 Tu et al.
7,458,953 B2 12/2008 Peyman
7,468,065 B2 12/2008 Weber et al.
7,481,816 B2 1/2009 Richter et al.
7,488,303 B1 2/2009 Haffner et al.
7,524,298 B2 4/2009 Gharib et al.
7,563,241 B2 7/2009 Tu et al.
7,594,899 B2 9/2009 Pinchuk et al.
7,625,384 B2 12/2009 Eriksson et al.
7,658,729 B2 2/2010 Hull
7,670,310 B2 3/2010 Yaron et al.
7,678,065 B2 3/2010 Haffner et al.
7,708,711 B2 5/2010 Tu et al.
7,717,872 B2 5/2010 Shetty
7,722,549 B2 5/2010 Nakao
7,740,604 B2 6/2010 Schieber et al.
7,794,437 B2 9/2010 Humayun et al.
7,815,592 B2 10/2010 Coroneo
7,824,372 B1 11/2010 Kurup
7,837,644 B2 11/2010 Pinchuk et al.
7,850,637 B2 12/2010 Lynch et al.
7,850,638 B2 12/2010 Theodore Coroneo
7,857,782 B2 12/2010 Tu et al.
7,862,531 B2 1/2011 Yaron et al.
7,867,186 B2 1/2011 Haffner et al.
7,867,205 B2 1/2011 Bergheim et al.
7,879,001 B2 2/2011 Haffner et al.
7,879,079 B2 2/2011 Tu et al.
7,892,282 B2 2/2011 Shepherd
7,951,155 B2 5/2011 Smedley et al.
7,998,497 B2 8/2011 De Juan, Jr. et al.
8,003,124 B2 8/2011 Varner et al.
8,007,459 B2 8/2011 Haffner et al.
8,034,016 B2 10/2011 Yaron et al.
8,062,244 B2 11/2011 Tu et al.
8,075,511 B2 12/2011 Tu et al.
8,109,896 B2 2/2012 Nissan et al.
8,118,768 B2 2/2012 Tu et al.
8,128,588 B2 3/2012 Coroneo
8,142,364 B2 3/2012 Haffner et al.
8,152,752 B2 4/2012 Lynch et al.
8,167,939 B2 5/2012 Silvestrini et al.
8,172,899 B2 5/2012 Silvestrini et al.
8,262,726 B2 9/2012 Silvestrini et al.
8,267,882 B2 9/2012 Euteneuer et al.
8,273,050 B2 9/2012 Bergheim et al.
8,277,437 B2 10/2012 Saal et al.
8,282,592 B2 10/2012 Schieber et al.
8,287,494 B2 10/2012 Ma
8,287,882 B2 10/2012 Gudkov et al.
8,308,701 B2 11/2012 Horvath et al.
8,313,454 B2 11/2012 Yaron et al.
8,333,742 B2 12/2012 Bergheim et al.
8,337,393 B2 12/2012 Silverstrini et al.
8,337,445 B2 12/2012 Tu et al.
8,337,509 B2 12/2012 Schieber et al.
8,348,877 B2 1/2013 Tu et al.
8,372,026 B2 2/2013 Schieber et al.
8,377,122 B2 2/2013 Silvestrini et al.
8,388,568 B2 3/2013 Lynch et al.
8,414,518 B2 4/2013 Schieber et al.
8,425,449 B2 4/2013 Wardle et al.
8,444,588 B2 5/2013 Yablonski
8,444,589 B2 5/2013 Silvestrini
8,454,582 B2 6/2013 Dejuan et al.
8,460,242 B2 6/2013 Paques et al.
8,485,000 B2 7/2013 Lim et al.
8,486,000 B2 7/2013 Coroneo
8,486,086 B2 7/2013 Yaron et al.
8,506,515 B2 8/2013 Burns et al.
8,508,515 B2 8/2013 Wang et al.
8,512,404 B2 8/2013 Frion et al.
8,529,492 B2 9/2013 Clauson et al.
8,529,494 B2 9/2013 Euteneuer et al.
8,535,333 B2 9/2013 De Juan, Jr. et al.
8,545,430 B2 10/2013 Silvestrini
8,551,166 B2 10/2013 Schieber et al.
8,574,294 B2 11/2013 Silvestrini et al.
8,579,846 B2 11/2013 Tu et al.
8,585,629 B2 11/2013 Grabner et al.
8,597,301 B2 12/2013 Mitchell
8,608,632 B1 12/2013 Brigatti et al.
8,663,303 B2 3/2014 Horvath et al.
8,721,702 B2 5/2014 Romoda et al.
8,758,290 B2 6/2014 Horvath et al.
8,765,210 B2 7/2014 Romoda et al.
8,801,766 B2 8/2014 Reitsamer et al.
8,828,070 B2 9/2014 Romoda et al.
8,852,136 B2 10/2014 Horvath et al.
8,852,137 B2 10/2014 Horvath et al.
8,852,256 B2 10/2014 Horvath et al.
8,974,511 B2 3/2015 Horvath et al.
9,017,276 B2 4/2015 Horvath et al.
9,044,301 B1 6/2015 Pinchuk et al.
9,095,411 B2 8/2015 Horvath et al.
9,095,413 B2 8/2015 Romoda et al.
9,113,994 B2 8/2015 Romoda et al.
9,125,723 B2 9/2015 Horvath et al.
9,168,172 B1 10/2015 Berdahl
9,192,516 B2 11/2015 Horvath et al.
9,271,869 B2 3/2016 Horvath et al.
9,283,116 B2 3/2016 Romoda et al.
9,326,891 B2 5/2016 Horvath et al.
9,393,153 B2 7/2016 Horvath et al.
9,730,056 B2 8/2017 Nneke et al.
9,808,373 B2 11/2017 Horvath et al.
10,085,884 B2 10/2018 Reitsamer et al.
10,369,048 B2 8/2019 Horvath et al.
10,387,598 B1 8/2019 Gregor et al.
10,952,898 B2 3/2021 Romoda et al.
2001/0007075 A1 7/2001 Hjertman et al.
2001/0025150 A1 9/2001 De Juan et al.
2001/0056254 A1 12/2001 Cragg et al.
2002/0087149 A1 7/2002 McCary
2002/0099434 A1 7/2002 Buscemi et al.
2002/0133168 A1 9/2002 Smedley et al.
2002/0143284 A1 10/2002 Tu et al.
2003/0015203 A1 1/2003 Makower et al.
2003/0050574 A1 3/2003 Krueger
2003/0055372 A1 3/2003 Lynch et al.
2003/0060752 A1 3/2003 Bergheim et al.
2003/0093084 A1 5/2003 Nissan et al.
2003/0097053 A1 5/2003 Itoh
2003/0097151 A1 5/2003 Smedley et al.
2003/0187383 A1 10/2003 Weber et al.
2003/0212383 A1 11/2003 Cote et al.
2003/0229303 A1 12/2003 Haffner et al.
2003/0236483 A1 12/2003 Ren

(56) References Cited

U.S. PATENT DOCUMENTS

2003/0236484 A1 12/2003 Lynch et al.
2004/0024345 A1 2/2004 Gharib et al.
2004/0077987 A1 4/2004 Rapacki et al.
2004/0111050 A1 6/2004 Smedley et al.
2004/0147870 A1 7/2004 Burns et al.
2004/0154946 A1 8/2004 Solovay et al.
2004/0158269 A1 8/2004 Holman
2004/0193262 A1 9/2004 Shadduck
2004/0199130 A1 10/2004 Chornenky et al.
2004/0210209 A1 10/2004 Yeung et al.
2004/0215133 A1 10/2004 Weber et al.
2004/0216749 A1 11/2004 Tu
2004/0225250 A1 11/2004 Yablonski
2004/0236343 A1 11/2004 Taylor et al.
2004/0238343 A1 12/2004 Kuo et al.
2004/0254521 A1 12/2004 Simon
2004/0260227 A1 12/2004 Lisk et al.
2005/0049578 A1 3/2005 Tu et al.
2005/0101967 A1 5/2005 Weber et al.
2005/0119601 A9 6/2005 Lynch et al.
2005/0143363 A1 6/2005 De Juan et al.
2005/0177183 A1 8/2005 Thorne et al.
2005/0246023 A1 11/2005 Yeung
2005/0250788 A1 11/2005 Tu et al.
2005/0261624 A1 11/2005 Wilcox
2005/0267398 A1 12/2005 Protopsaltis et al.
2005/0271704 A1 12/2005 Tu et al.
2005/0277864 A1 12/2005 Haffner et al.
2006/0032507 A1 2/2006 Tu
2006/0052721 A1 3/2006 Dunker et al.
2006/0064112 A1 3/2006 Perez
2006/0106370 A1 5/2006 Baerveldt et al.
2006/0110428 A1 5/2006 Dejuan et al.
2006/0116625 A1 6/2006 Renati et al.
2006/0142781 A1 6/2006 Pynson et al.
2006/0147643 A1 7/2006 Volkov et al.
2006/0149194 A1 7/2006 Conston et al.
2006/0155238 A1 7/2006 Shields
2006/0173397 A1 8/2006 Tu et al.
2006/0173446 A1 8/2006 Dacquay et al.
2006/0189932 A1 8/2006 Yang et al.
2006/0200113 A1 9/2006 Haffner et al.
2006/0217740 A1 9/2006 Ghannoum
2006/0241411 A1 10/2006 Field et al.
2006/0241650 A1 10/2006 Weber et al.
2007/0010843 A1 1/2007 Green
2007/0027537 A1 2/2007 Castillejos
2007/0093783 A1 4/2007 Kugler et al.
2007/0118065 A1 5/2007 Pinchuk et al.
2007/0141116 A1 6/2007 Pinchuk et al.
2007/0172903 A1 7/2007 Toner et al.
2007/0179471 A1 8/2007 Christian et al.
2007/0191863 A1 8/2007 De Juan et al.
2007/0202186 A1 8/2007 Yamamoto et al.
2007/0233037 A1 10/2007 Gifford et al.
2007/0263172 A1 11/2007 Mura
2007/0269487 A1 11/2007 De Juan et al.
2007/0270775 A1 11/2007 Miller et al.
2007/0276315 A1 11/2007 Haffner et al.
2007/0276316 A1 11/2007 Haffner et al.
2007/0282244 A1 12/2007 Tu et al.
2007/0282245 A1 12/2007 Tu et al.
2007/0293807 A1 12/2007 Lynch et al.
2007/0293872 A1 12/2007 Peyman
2007/0299459 A1 12/2007 Way et al.
2008/0015488 A1 1/2008 Tu et al.
2008/0015633 A1 1/2008 Abbott et al.
2008/0027304 A1 1/2008 Pardo et al.
2008/0045878 A1 2/2008 Bergheim et al.
2008/0057106 A1 3/2008 Erickson et al.
2008/0058717 A1 3/2008 Spector
2008/0077071 A1 3/2008 Yaron et al.
2008/0091224 A1 4/2008 Griffis et al.
2008/0108933 A1 5/2008 Yu et al.
2008/0125691 A1 5/2008 Yaron et al.
2008/0147001 A1 6/2008 Al-Marashi et al.
2008/0181929 A1 7/2008 Robinson et al.
2008/0183121 A2 7/2008 Smedley et al.
2008/0195027 A1 8/2008 Coroneo
2008/0200860 A1 8/2008 Tu et al.
2008/0228127 A1 9/2008 Burns et al.
2008/0234624 A2 9/2008 Bergheim et al.
2008/0249467 A1 10/2008 Burnett et al.
2008/0281277 A1 11/2008 Thyzel
2008/0289635 A1 11/2008 Hull
2008/0312661 A1 12/2008 Downer et al.
2009/0036818 A1 2/2009 Grahn et al.
2009/0036819 A1 2/2009 Tu et al.
2009/0043321 A1 2/2009 Conston et al.
2009/0076436 A2 3/2009 Gharib et al.
2009/0082860 A1 3/2009 Schieber et al.
2009/0082862 A1 3/2009 Schieber et al.
2009/0082863 A1 3/2009 Schieber et al.
2009/0092654 A1 4/2009 Juan, Jr. et al.
2009/0099552 A1 4/2009 Levy et al.
2009/0099626 A1 4/2009 De Juan, Jr. et al.
2009/0104243 A1 4/2009 Utkhede et al.
2009/0105749 A1 4/2009 De Juan et al.
2009/0124973 A1 5/2009 D'Agostino et al.
2009/0132040 A1 5/2009 Frion et al.
2009/0137983 A1 5/2009 Bergheim et al.
2009/0138022 A1 5/2009 Tu et al.
2009/0138081 A1 5/2009 Bergheim et al.
2009/0143712 A1 6/2009 Tu et al.
2009/0171366 A1* 7/2009 Tanaka .................... A61F 2/167
606/107
2009/0177138 A1 7/2009 Brown et al.
2009/0182421 A1 7/2009 Silvestrini et al.
2009/0204053 A1 8/2009 Nissan et al.
2009/0209910 A1 8/2009 Kugler et al.
2009/0216106 A1 8/2009 Takii
2009/0227934 A1 9/2009 Euteneuer et al.
2009/0264813 A1 10/2009 Chang
2009/0270890 A1 10/2009 Robinson et al.
2009/0281520 A1 11/2009 Highley et al.
2009/0284813 A1 11/2009 Saito
2009/0287136 A1 11/2009 Castillejos
2010/0004499 A1 1/2010 Brigatti et al.
2010/0004580 A1 1/2010 Lynch et al.
2010/0004581 A1 1/2010 Brigatti et al.
2010/0010414 A1 1/2010 Bergheim et al.
2010/0010416 A1 1/2010 Juan, Jr. et al.
2010/0030146 A1 2/2010 Kakish et al.
2010/0056979 A1 3/2010 Smedley et al.
2010/0063478 A1 3/2010 Selkee
2010/0063512 A1 3/2010 Braga et al.
2010/0083478 A1 4/2010 Griggs et al.
2010/0087774 A1 4/2010 Haffner et al.
2010/0087832 A1 4/2010 Seyboth
2010/0090441 A1 4/2010 Stettler
2010/0098772 A1 4/2010 Robinson et al.
2010/0100104 A1 4/2010 Yu et al.
2010/0106073 A1 4/2010 Haffner et al.
2010/0114006 A1 5/2010 Baerveldt
2010/0119696 A1 5/2010 Yu et al.
2010/0121248 A1 5/2010 Yu et al.
2010/0121249 A1 5/2010 Yu et al.
2010/0121342 A1 5/2010 Schieber et al.
2010/0134759 A1 6/2010 Silvestrini et al.
2010/0137981 A1 6/2010 Silvestrini et al.
2010/0152641 A1 6/2010 Yablonski
2010/0173866 A1 7/2010 Hee et al.
2010/0185138 A1 7/2010 Yaron et al.
2010/0191103 A1 7/2010 Stamper et al.
2010/0191224 A1 7/2010 Butcher
2010/0217206 A1 8/2010 Lum et al.
2010/0222733 A1 9/2010 Schieber et al.
2010/0234790 A1 9/2010 Tu et al.
2010/0234791 A1 9/2010 Lynch et al.
2010/0241046 A1 9/2010 Pinchuk et al.
2010/0249497 A1 9/2010 Peine et al.
2010/0249691 A1 9/2010 Van Der Mooren et al.
2010/0274258 A1 10/2010 Silvestrini et al.
2010/0274259 A1 10/2010 Yaron et al.

(56) References Cited

U.S. PATENT DOCUMENTS

| | | | |
|---|---|---|---|
| 2010/0280317 | A1 | 11/2010 | Silvestrini et al. |
| 2010/0292642 | A1 | 11/2010 | Kurup |
| 2010/0312254 | A1 | 12/2010 | Downer et al. |
| 2010/0328606 | A1 | 12/2010 | Peyman |
| 2011/0009872 | A1 | 1/2011 | Mistry et al. |
| 2011/0009874 | A1 | 1/2011 | Wardle et al. |
| 2011/0009958 | A1 | 1/2011 | Wardle et al. |
| 2011/0015645 | A1 | 1/2011 | Liu et al. |
| 2011/0028883 | A1 | 2/2011 | Juan, Jr. et al. |
| 2011/0028884 | A1 | 2/2011 | Theodore Coroneo |
| 2011/0028983 | A1 | 2/2011 | Silvestrini et al. |
| 2011/0046536 | A1 | 2/2011 | Stegmann et al. |
| 2011/0087148 | A1 | 4/2011 | Silvestrini et al. |
| 2011/0087149 | A1 | 4/2011 | Theodore Coroneo |
| 2011/0087150 | A1 | 4/2011 | Theodore Coroneo |
| 2011/0087151 | A1 | 4/2011 | Theodore Coroneo |
| 2011/0092878 | A1 | 4/2011 | Tu et al. |
| 2011/0098627 | A1 | 4/2011 | Wilcox |
| 2011/0098629 | A1 | 4/2011 | Juan, Jr. et al. |
| 2011/0098809 | A1 | 4/2011 | Wardle et al. |
| 2011/0105986 | A1 | 5/2011 | Bronstein et al. |
| 2011/0105987 | A1 | 5/2011 | Bergheim et al. |
| 2011/0105990 | A1 | 5/2011 | Silvestrini |
| 2011/0112546 | A1 | 5/2011 | Juan, Jr. et al. |
| 2011/0118745 | A1 | 5/2011 | Yu et al. |
| 2011/0118835 | A1 | 5/2011 | Silvestrini et al. |
| 2011/0152749 | A1 | 6/2011 | Touchard et al. |
| 2011/0159073 | A1 | 6/2011 | Dejuan et al. |
| 2011/0196281 | A1 | 8/2011 | Lynch et al. |
| 2011/0230890 | A1 | 9/2011 | Thyzel |
| 2011/0234976 | A1 | 9/2011 | Kocaoglu et al. |
| 2011/0238075 | A1 | 9/2011 | Clauson et al. |
| 2011/0245753 | A1 | 10/2011 | Sunalp |
| 2011/0276131 | A1 | 11/2011 | De Juan, Jr. et al. |
| 2011/0306915 | A1 | 12/2011 | De Juan, Jr. et al. |
| 2011/0319806 | A1 | 12/2011 | Wardle |
| 2012/0016286 | A1 | 1/2012 | Silvestrini et al. |
| 2012/0022429 | A1 | 1/2012 | Silvestrini et al. |
| 2012/0035524 | A1 | 2/2012 | Silvestrini |
| 2012/0035525 | A1 | 2/2012 | Silvestrini |
| 2012/0053505 | A1 | 3/2012 | Yaron et al. |
| 2012/0071809 | A1 | 3/2012 | Tu et al. |
| 2012/0078158 | A1 | 3/2012 | Haffner et al. |
| 2012/0078362 | A1 | 3/2012 | Haffner et al. |
| 2012/0109040 | A1 | 5/2012 | Smedley et al. |
| 2012/0123315 | A1 | 5/2012 | Horvath et al. |
| 2012/0123316 | A1 | 5/2012 | Horvath et al. |
| 2012/0123317 | A1 | 5/2012 | Horvath et al. |
| 2012/0123430 | A1 | 5/2012 | Horvath et al. |
| 2012/0123433 | A1 | 5/2012 | Horvath et al. |
| 2012/0123434 | A1 | 5/2012 | Grabner et al. |
| 2012/0123435 | A1 | 5/2012 | Romoda et al. |
| 2012/0123436 | A1 | 5/2012 | Reitsamer et al. |
| 2012/0123437 | A1 | 5/2012 | Horvath et al. |
| 2012/0123438 | A1 | 5/2012 | Horvath et al. |
| 2012/0123439 | A1 | 5/2012 | Romoda et al. |
| 2012/0123440 | A1 | 5/2012 | Horvath et al. |
| 2012/0136439 | A1 | 5/2012 | Schieber et al. |
| 2012/0150129 | A1 | 6/2012 | Jin et al. |
| 2012/0165720 | A1 | 6/2012 | Horvath et al. |
| 2012/0165721 | A1 | 6/2012 | Grabner et al. |
| 2012/0165722 | A1 | 6/2012 | Horvath et al. |
| 2012/0165723 | A1 | 6/2012 | Horvath et al. |
| 2012/0165933 | A1 | 6/2012 | Haffner et al. |
| 2012/0179087 | A1 | 7/2012 | Schieber et al. |
| 2012/0187594 | A1 | 7/2012 | Utkhede et al. |
| 2012/0197175 | A1 | 8/2012 | Horvath et al. |
| 2012/0215241 | A1 | 8/2012 | Trees et al. |
| 2012/0220917 | A1 | 8/2012 | Silvestrini et al. |
| 2012/0226150 | A1 | 9/2012 | Balicki et al. |
| 2012/0253258 | A1 | 10/2012 | Tu et al. |
| 2012/0259195 | A1 | 10/2012 | Haffner et al. |
| 2012/0310137 | A1 | 12/2012 | Silvestrini |
| 2012/0323159 | A1 | 12/2012 | Wardle et al. |
| 2013/0096483 | A1 | 4/2013 | Dacquay |
| 2013/0149429 | A1 | 6/2013 | Romoda et al. |
| 2013/0150770 | A1 | 6/2013 | Horvath et al. |
| 2013/0150773 | A1 | 6/2013 | Nissan et al. |
| 2013/0158462 | A1 | 6/2013 | Wardle et al. |
| 2013/0158574 | A1 | 6/2013 | Yi et al. |
| 2013/0184631 | A1 | 7/2013 | Pinchuk |
| 2013/0211312 | A1 | 8/2013 | Gelvin |
| 2013/0211314 | A1 | 8/2013 | Venkatraman et al. |
| 2013/0237958 | A1 | 9/2013 | Arrigo |
| 2013/0245573 | A1 | 9/2013 | De Juan, Jr. et al. |
| 2013/0253406 | A1 | 9/2013 | Horvath et al. |
| 2013/0253528 | A1 | 9/2013 | Haffner et al. |
| 2013/0267887 | A1* | 10/2013 | Kahook .............. A61F 9/00781 604/9 |
| 2013/0281817 | A1 | 10/2013 | Schaller et al. |
| 2013/0281907 | A1 | 10/2013 | Wardle et al. |
| 2013/0281908 | A1 | 10/2013 | Schaller et al. |
| 2013/0289467 | A1 | 10/2013 | Haffner et al. |
| 2013/0325024 | A1 | 12/2013 | Nissan et al. |
| 2013/0345515 | A1 | 12/2013 | Fitzmaurice |
| 2014/0066833 | A1 | 3/2014 | Yaron et al. |
| 2014/0081195 | A1 | 3/2014 | Clauson et al. |
| 2014/0135916 | A1 | 5/2014 | Clauson et al. |
| 2014/0163448 | A1 | 6/2014 | Lind et al. |
| 2014/0180189 | A1 | 6/2014 | Horvath et al. |
| 2014/0213958 | A1 | 7/2014 | Clauson et al. |
| 2014/0236065 | A1 | 8/2014 | Romoda et al. |
| 2014/0236066 | A1 | 8/2014 | Horvath et al. |
| 2014/0236067 | A1 | 8/2014 | Horvath et al. |
| 2014/0243730 | A1 | 8/2014 | Horvath |
| 2014/0243975 | A1* | 8/2014 | Saidi ......................... A61F 5/08 623/10 |
| 2014/0272102 | A1 | 9/2014 | Romoda et al. |
| 2014/0275923 | A1 | 9/2014 | Haffner et al. |
| 2014/0276332 | A1 | 9/2014 | Crimaldi et al. |
| 2014/0277349 | A1 | 9/2014 | Vad |
| 2014/0277429 | A1 | 9/2014 | Kuzma et al. |
| 2014/0287077 | A1 | 9/2014 | Romoda et al. |
| 2014/0303544 | A1 | 10/2014 | Haffner et al. |
| 2014/0323995 | A1 | 10/2014 | Clauson et al. |
| 2014/0343476 | A1 | 11/2014 | Penhasi |
| 2014/0364789 | A1 | 12/2014 | Schaller |
| 2014/0371651 | A1 | 12/2014 | Pinchuk |
| 2014/0378886 | A1 | 12/2014 | De Juan, Jr. et al. |
| 2015/0005689 | A1 | 1/2015 | Horvath et al. |
| 2015/0011926 | A1 | 1/2015 | Reitsamer et al. |
| 2015/0027866 | A1 | 1/2015 | Morimoto et al. |
| 2015/0038893 | A1 | 2/2015 | Haffner et al. |
| 2015/0045714 | A1 | 2/2015 | Horvath et al. |
| 2015/0057591 | A1 | 2/2015 | Horvath et al. |
| 2015/0133946 | A1 | 5/2015 | Horvath et al. |
| 2015/0238687 | A1 | 8/2015 | Novakovic et al. |
| 2015/0265469 | A1 | 9/2015 | Olson et al. |
| 2015/0290035 | A1 | 10/2015 | Horvath et al. |
| 2015/0374545 | A1 | 12/2015 | Horvath et al. |
| 2016/0038338 | A1 | 2/2016 | Rangel-Friedman et al. |
| 2016/0074211 | A1 | 3/2016 | Ko et al. |
| 2016/0089513 | A1 | 3/2016 | Ishida |
| 2016/0101269 | A1 | 4/2016 | Benz |
| 2016/0135993 | A1 | 5/2016 | Horvath et al. |
| 2016/0135994 | A1 | 5/2016 | Romoda et al. |
| 2016/0158063 | A1 | 6/2016 | Romoda et al. |
| 2016/0168063 | A1 | 6/2016 | Stanislaus et al. |
| 2016/0249947 | A1 | 9/2016 | Castanon et al. |
| 2016/0250071 | A1 | 9/2016 | Horvath et al. |
| 2016/0256317 | A1 | 9/2016 | Horvath et al. |
| 2016/0256318 | A1 | 9/2016 | Horvath et al. |
| 2016/0256319 | A1 | 9/2016 | Horvath et al. |
| 2016/0256320 | A1 | 9/2016 | Horvath et al. |
| 2016/0256321 | A1 | 9/2016 | Horvath et al. |
| 2016/0256322 | A1 | 9/2016 | Horvath et al. |
| 2016/0256323 | A1 | 9/2016 | Horvath et al. |
| 2016/0278982 | A1 | 9/2016 | Horvath et al. |
| 2016/0331902 | A1 | 11/2016 | Carlyon |
| 2016/0354244 | A1 | 12/2016 | Horvath et al. |
| 2016/0354245 | A1 | 12/2016 | Horvath et al. |
| 2017/0086821 | A1 | 3/2017 | Meade et al. |
| 2017/0172797 | A1 | 6/2017 | Horvath et al. |
| 2017/0172798 | A1 | 6/2017 | Horvath et al. |

(56) References Cited

U.S. PATENT DOCUMENTS

| | | | |
|---|---|---|---|
| 2017/0172799 | A1 | 6/2017 | Horvath |
| 2017/0172800 | A1 | 6/2017 | Romoda et al. |
| 2017/0348150 | A1 | 12/2017 | Horvath et al. |
| 2018/0008464 | A1 | 1/2018 | Horvath et al. |
| 2018/0199797 | A1 | 7/2018 | London Brown et al. |
| 2019/0030285 | A1 | 1/2019 | Prabhu et al. |
| 2019/0054272 | A1 | 2/2019 | Tal |
| 2019/0069770 | A1 | 3/2019 | Bourget et al. |
| 2019/0133826 | A1 | 5/2019 | Horvath et al. |
| 2019/0240069 | A1 | 8/2019 | Horvath et al. |
| 2019/0290314 | A1 | 9/2019 | Gemer et al. |
| 2020/0046213 | A1 | 2/2020 | Bendory et al. |
| 2020/0054353 | A1 | 2/2020 | Yun et al. |
| 2020/0246188 | A1 | 8/2020 | Horvath et al. |
| 2021/0196338 | A1* | 7/2021 | Dam-Huisman ....... A61F 9/007 |
| 2024/0390187 | A1 | 11/2024 | Haffner |

FOREIGN PATENT DOCUMENTS

| | | | |
|---|---|---|---|
| CN | 1794957 | A | 6/2006 |
| CN | 1909859 | A | 2/2007 |
| CN | 101677823 | A | 3/2010 |
| CN | 102170840 | A | 8/2011 |
| CN | 102481171 | A | 5/2012 |
| CN | 102510746 | A | 6/2012 |
| CN | 103313751 | A | 9/2013 |
| CN | 105899170 | A | 8/2016 |
| CN | 106999294 | A | 8/2017 |
| CO | 16139950 | A | 5/2016 |
| GB | 2296663 | A | 7/1996 |
| JP | 2007181604 | A | 7/2007 |
| JP | 2009523540 | A | 6/2009 |
| JP | 2012030128 | A | 2/2012 |
| JP | 2012527318 | A | 11/2012 |
| JP | 2012529350 | A | 11/2012 |
| JP | 2012532692 | A | 12/2012 |
| JP | 2014500758 | A | 1/2014 |
| JP | 2015110017 | A | 6/2015 |
| JP | 2015517836 | A | 6/2015 |
| JP | WO2013137208 | A1 | 8/2015 |
| JP | 2015157051 | A | 9/2015 |
| JP | 2016537153 | A | 12/2016 |
| JP | 2017104737 | A | 6/2017 |
| JP | 2017140494 | A | 8/2017 |
| RU | 2313315 | C2 | 12/2007 |
| RU | 2482822 | C2 | 5/2013 |
| WO | 1994013234 | A1 | 6/1994 |
| WO | 1994021205 | A1 | 9/1994 |
| WO | 1995008310 | A1 | 3/1995 |
| WO | 1998023237 | A1 | 6/1998 |
| WO | 2000056255 | A1 | 9/2000 |
| WO | 2001050943 | A2 | 7/2001 |
| WO | 2002074052 | A2 | 9/2002 |
| WO | 2007087061 | A3 | 12/2007 |
| WO | 2008005873 | A3 | 7/2008 |
| WO | 2010003011 | A1 | 1/2010 |
| WO | 2011155922 | A1 | 12/2011 |
| WO | 2013151904 | A1 | 10/2013 |
| WO | 2014150292 | A1 | 9/2014 |
| WO | 2015000943 | A2 | 1/2015 |
| WO | 2015073705 | A1 | 5/2015 |
| WO | 2016023942 | A1 | 2/2016 |
| WO | 2016159999 | A1 | 10/2016 |
| WO | 2016196841 | A1 | 12/2016 |
| WO | 2017040855 | A1 | 3/2017 |
| WO | 2017184881 | A1 | 10/2017 |
| WO | 2021168364 | A1 | 8/2021 |

OTHER PUBLICATIONS

PCT/US2021/018922 International Search Report and Written Opinion, dated Aug. 2, 2021, 17 pages.

Saudia Arabia Office Action dated Sep. 19, 2024 from related SA Application No. 522440219 (7 pages).

Aquesys Inc., Extended Eurpoean Search Report with mailing date of Jul. 26, 2024 from related EP Application No. 24169164.1; 6 pages.

* cited by examiner

BI-MODAL INTRAOCULAR SHUNT INSERTER

CROSS-REFERENCE TO RELATED APPLICATIONS

This application claims the benefit of U.S. Provisional Application No. 62/979,353, filed Feb. 20, 2020, the entirety of which is incorporated herein by reference.

BACKGROUND

Field of the Inventions

The present inventions relate to intraocular shunt inserters and their use in methods of implanting an intraocular shunt into an eye.

Description of the Related Art

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness.

Glaucoma may be treated in a number of different ways. One manner of treatment involves delivery of drugs such as beta-blockers or prostaglandins to the eye to either reduce production of aqueous humor or increase flow of aqueous humor from an anterior chamber of the eye. Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Such fluid flow pathways allow for aqueous humor to exit the anterior chamber.

SUMMARY

The importance of lowering intraocular pressure in delaying glaucomatous progression is well documented. When drug therapy fails, or is not tolerated, surgical intervention is warranted. There are various surgical filtration methods for lowering intraocular pressure by creating a fluid flow-path between the anterior chamber and the subconjunctival tissue. In one particular method, an intraocular shunt is implanted with an inserter by directing a needle, which holds the shunt through the cornea, across the anterior chamber, and through the trabecular meshwork and sclera, and into the subconjunctival space. See, for example, U.S. Pat. No. 6,544,249, U.S. Patent Application Publication No. 2008/0108933, and U.S. Pat. No. 6,007,511, the entireties of each of which are incorporated herein by reference.

Clinicians may implant the intraocular shunt using an ab externo procedure or an ab interno procedure, depending on the needs of the patient and the selected treatment. In an ab externo approach, the clinician may enter through the conjunctiva and inwards through the sclera, as described in the present applicant's publications, including U.S. Pat. Nos. 10,470,927, and 10,463,537. In an ab interno approach, the clinician may enter through the cornea, across the anterior chamber, through the trabecular meshwork and sclera.

In accordance with an aspect of some embodiments disclosed herein is the realization that some clinicians may prefer to reposition a shunt relative to a bevel of the needle in preparation for surgery. For example, some clinicians may prefer to position the shunt in a certain location relative to a bevel of the needle when implanting the intraocular shunt using an ab interno procedure, but may prefer that the shunt be positioned at a different location relative to the bevel of the needle when performing an ab externo procedure. Moreover, certain anatomies, shunt types and/or materials, and/or procedures may require such repositioning, in order to enable the clinician to most advantageously deliver the shunt.

Further, in accordance with an aspect of some embodiments disclosed herein is the realization of the need for an intraocular shunt inserter that permits a clinician to quickly, reliably, and accurately reposition the shunt relative to the bevel of the needle according to their own preference, for performing different surgical techniques or approaches (e.g., ab externo procedure or ab interno), or in response to other shunt or patient factors and conditions.

Accordingly, the present disclosure contemplates these problems, provides solutions to these problems, and relates to the realization that precision can be increased while reducing operator effort, preparation time, cost, potential trauma to the patient, and surgery time, in some embodiments, implementing certain advantageous features in a shunt inserter.

Some embodiments disclosed herein provide an intraocular shunt inserter that includes a component driver including an actuation member, wherein the component driver elongates from a first length to a second length upon movement of the actuation member for changing a longitudinal relative position of a distal end portion of the plunger or a distal end portion of the needle. The first length of the component driver can position the shunt for ab externo treatment, and the second length of the component driver can position the shunt for ab interno treatment.

The component driver can be coupled to, part of, or control a movement or position of a plunger or needle of the inserter. Optionally, the inserter can include two component drivers, one component driver coupled to, part of, or control a movement or position of the plunger and another component driver coupled to, part of, or control a movement or position of the needle of the inserter.

Some embodiments disclosed herein provide an intraocular shunt inserter that includes a plunger driver coupled to a proximal end portion of the plunger, the plunger driver including an actuation member, wherein the plunger driver elongates from a first length to a second length upon movement of the actuation member for advancing the shunt relative to the bevel of the needle. The first length of the plunger driver can position the shunt for ab externo treatment, and the second length of the plunger driver can position the shunt for ab interno treatment.

Some embodiments disclosed herein provide an intraocular shunt inserter that includes a needle driver coupled to a proximal end portion of the needle, the needle driver including an actuation member, wherein the plunger driver foreshortens from a first length to a second length upon movement of the actuation member for retracting the bevel of the needle relative to the shunt. The first length of the needle driver can position the needle relative to the shunt for ab externo treatment, and the second length of the needle drive can position needle relative to the shunt for ab interno treatment.

Optionally, the actuation member can include an oblong cam, wherein the oblong cam is rotatable within a body of the plunger driver about an axis oriented perpendicular relative to a longitudinal axis of the inserter. The oblong cam can include a major axis and a minor axis, and the plunger driver elongates from the first length to the second length by rotating the oblong cam to align the major axis with the longitudinal axis of the inserter. The actuation member can positively displace the plunger driver from the first length to the second length.

Some embodiments disclosed herein provide an intraocular shunt inserter that includes a needle driver and a plunger driver, and an actuation mechanism to change the length of both the needle driver and the length of the plunger driver to adapt the inserter for either ab externo procedures or ab interno procedures. The plunger driver and the needle driver can move in opposing directions upon actuation.

Optionally, the inserter can include a removable key to releasably engage with the actuation member. The removable key can also prevent release of the shunt before intended.

An operator can operate the inserter by moving a plunger driver actuation member to change a plunger driver from a first plunger driver length to a second plunger driver length to advance the shunt relative to the bevel of the needle, The operator can also operate the inserter by moving a needle driver actuation member to change a needle driver from a first needle driver length to a second needle driver length to move the bevel of the needle relative to the shunt.

Optionally, the operator can rotate one or more cam mechanisms to extend the plunger driver and/or retract the needle driver, positioning the shunt relative to the bevel of the needle.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

Figure 1:
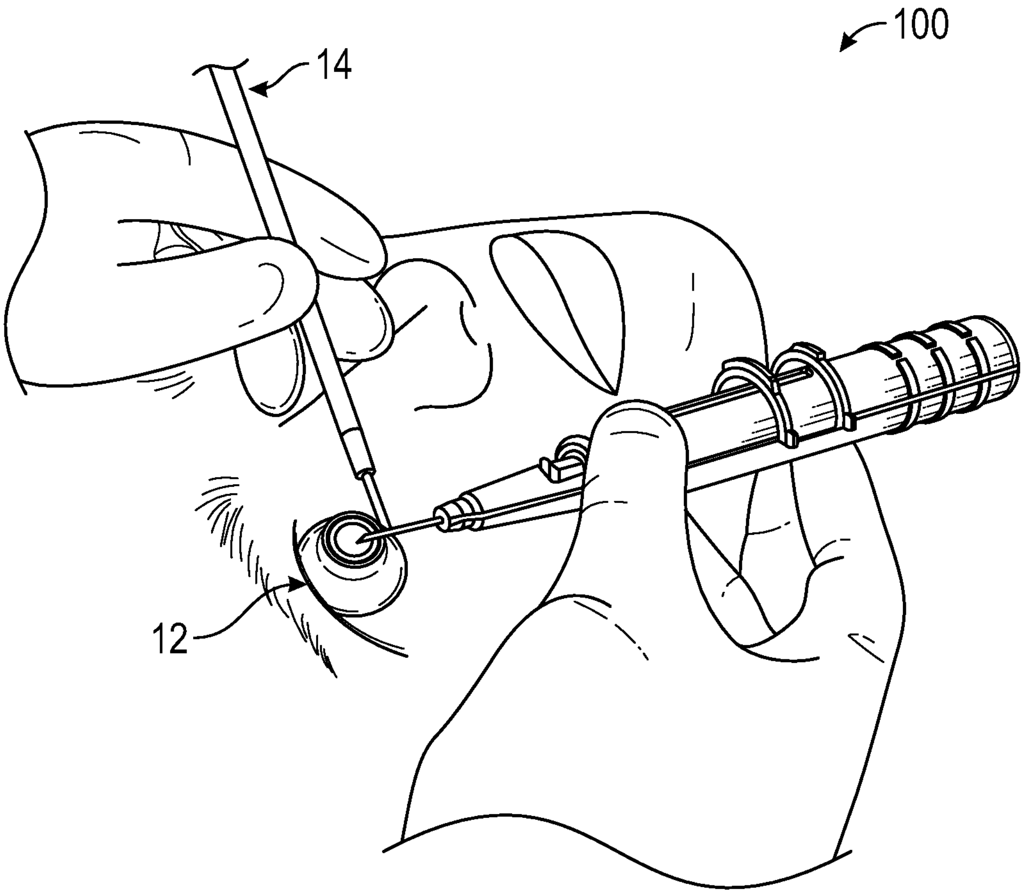
FIG. 1 is a schematic view of a procedure for implanting an intraocular shunt into an eye using an inserter, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Glaucoma is a disease in which the optic nerve is damaged, leading to progressive, irreversible loss of vision. It is typically associated with increased pressure of the fluid (i.e., aqueous humor) in the eye. Untreated glaucoma leads to permanent damage of the optic nerve and resultant visual field loss, which can progress to blindness. Once lost, this damaged visual field cannot be recovered.

In conditions of glaucoma, the pressure of the aqueous humor in the eye (anterior chamber) increases and this resultant increase of pressure can cause damage to the vascular system at the back of the eye and especially to the optic nerve. The treatment of glaucoma and other diseases that lead to elevated pressure in the anterior chamber involves relieving pressure within the anterior chamber to a normal level.

Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Various structures and/or regions of the eye having lower pressure that have been targeted for aqueous humor drainage include Schlemm's canal, the subconjunctival space, the episcleral vein, the suprachoroidal space, the intra-Tenon's adhesion space, and the subarachnoid space. Shunts may be implanted using an ab externo approach (e.g., entering through the conjunctiva and inwards through the sclera) or an ab interno approach (e.g., entering through the cornea, across the anterior chamber, through the trabecular meshwork and sclera). For example, ab externo approaches for implanting an intraocular shunt in the subconjunctival space are shown for example in Horvath et al. (U.S. Pat. No. 10,470,927) and Horvath et al. (U.S. Patent Application Publication No. 2017/0348150), the contents of each which are incorporated by reference herein in its entirety. For example, ab interno approaches for implanting an intraocular shunt in the subconjunctival space are shown for example in Yu et al. (U.S. Pat. No. 6,544,249 and U.S. Patent Application Publication No. 2008/0108933) and Prywes (U.S. Pat. No. 6,007,511), the contents of each of which are incorporated by reference herein in its entirety.

Some methods can involve inserting into the eye a hollow shaft configured to hold an intraocular shunt. In some embodiments, the hollow shaft can be a component of a deployment device that may deploy the intraocular shunt. The hollow shaft can be coupled to a deployment device or be part of the deployment device itself. The deployment devices can include devices such as those as described in co-owned U.S. Pat. Nos. 9,585,790, 8,721,792, 8,852,136, and U.S. Patent Application Publication No. 2012/0123434, filed on Nov. 15, 2010, the contents of each of which are incorporated by reference herein in their entireties.

In accordance with some embodiments, the inserter can be advanced into the eye via an ab-interno or an ab-externo approach. Thereafter, the shunt can be deployed from the shaft into the eye such that the shunt forms a passage from the anterior chamber into an area of lower pressure, such as Schlemm's canal, the subconjunctival space, the episcleral vein, the suprachoroidal space, the intra-Tenon's adhesion space, the subarachnoid space, or other areas of the eye. The hollow shaft is then withdrawn from the eye. Methods for delivering and implanting bioabsorbable or permanent tubes or shunts, as well as implantation devices for performing such methods, are generally disclosed in applicant's applications, including U.S. Patent Application Publication Nos. 2012/0197175, 2015/0011926, and 2016/0354244, U.S. patent application Ser. No. 15/613,018, as well as in U.S. Pat. Nos. 6,007,511, 6,544,249, 8,852,136, and 9,585,790 each of which are incorporated by reference in their entireties.

Some methods can be conducted by making an incision in the eye prior to insertion of the deployment device. However, in some instances, the method may be conducted without making an incision in the eye prior to insertion of the deployment device. In some embodiments, the shaft that is connected to the deployment device has a sharpened point or tip. In some embodiments, the hollow shaft is a needle. Exemplary needles that may be used are commercially available from Terumo Medical Corp. (Elkington, Md.). In some embodiments, the needle can have a hollow interior and a beveled tip, and the intraocular shunt can be held within the hollow interior of the needle. In some embodiments, the needle can have a hollow interior and a triple ground point or tip.

Some methods can be conducted without needing to remove an anatomical portion or feature of the eye, including but not limited to the trabecular meshwork, the iris, the cornea, or aqueous humor. Some methods can be conducted without inducing substantial ocular inflammation, such as subconjunctival blebbing or endophthalmitis. Some methods can be achieved using an ab interno approach by inserting the hollow shaft configured to hold or carry the intraocular shunt as it is advanced through the cornea, across the anterior chamber, through the trabecular meshwork, and into the intra-scleral or intra-Tenon's adhesion space. However, some methods may be conducted using an ab externo approach.

In some methods conducted using an ab interno approach, the angle of entry through the cornea can be altered to affect optimal placement of the shunt in the intra-Tenon's adhesion space. The hollow shaft can be inserted into the eye at an angle above or below the corneal limbus, in contrast with entering through the corneal limbus.

For example, the hollow shaft can be inserted from about 0.25 mm to about 3.0 mm above the corneal limbus. The shaft can be inserted from about 0.5 mm to about 2.5 mm above the corneal limbus. The shaft can also be inserted from about 1.0 mm to about 2.0 mm above the corneal limbus, or any specific value within any of these ranges. For example, the hollow shaft can be inserted above the corneal limbus at distances of about: 1.0 mm, 1.1 mm, 1.2 mm, 1.3 mm, 1.4 mm, 1.5 mm, 1.6 mm, 1.7 mm, 1.8 mm, 1.9 mm, or 2.0 mm.

An ab interno approach or procedure may require or benefit from a shunt that is positioned differently relative to the bevel of the needle compared to the position of the shunt for ab externo procedures. For example, for an ab externo procedure it may be beneficial if the distal end of the shunt is positioned further proximal to the bevel of the needle than for an ab interno procedure. As noted above, existing inserters may not be able to, or may not easily allow for a clinician to reposition the shunt relative to the bevel of the needle prepare for an ab externo and/or ab interno procedure. The present disclosure provides various embodiments of methods and devices that can enable an operator easily position the shunt relative to the bevel of the needle to configure the inserter for either an ab externo procedure or an ab interno procedure.

Further, in some embodiments, placement of the shunt farther from the limbus at the exit site, as provided by an angle of entry above the limbus, can provide access to more lymphatic channels for drainage of aqueous humor, such as the episcleral lymphatic network, in addition to the conjunctival lymphatic system. A higher angle of entry also results in flatter placement in the intra-Tenon's adhesion space so that there is less bending of the shunt.

As discussed in U.S. Pat. No. 8,852,136, the entirety of which is incorporated herein by reference, in some embodiments, to ensure proper positioning and functioning of the intraocular shunt, the depth of penetration into the intra-Tenon's adhesion space may be important when performing some methods.

In some methods, the distal tip of the hollow shaft can pierce the sclera and intra-Tenon's adhesion space without coring, removing or causing major tissue distortion of the surrounding eye tissue. The shunt is then deployed from the shaft. Preferably, a distal portion of the hollow shaft (as opposed to the distal tip) completely enters the intra-Tenon's adhesion space before the shunt is deployed from the hollow shaft.

In accordance with some embodiments, the hollow shaft can comprise a flat bevel needle, such as a needle having a triple-ground point. The tip bevel can first pierce through the sclera and into the intra-Tenon's adhesion space by making a horizontal slit. In some methods, the needle can be advanced even further such that the entire flat bevel penetrates into the intra-Tenon's adhesion space, to spread and open the tissue to a full circular diameter.

Further, in accordance with an aspect of some methods, the intra-Tenon's channel can be urged open by the flat bevel portion of the needle so that the material around the opening is sufficiently stretched and a pinching of the shunt in that zone is avoided, thus preventing the shunt from failing due to the pinching or constriction. Full entry of the flat bevel into the intra-Tenon's adhesion space causes minor distortion and trauma to the local area. However, this area ultimately surrounds and conforms to the shunt once the shunt is deployed in the eye.

In some embodiments, the inserter can function as a one-handed device in order to allow an operator to keep their other hand on a fixation device that holds the eye, such as a hook. This can improve surgical control and placement accuracy and makes the surgery easier as well.

An illustration of a procedure for treating an eye 12 is shown in FIG. 1. FIG. 1 illustrates the use of a hook 14 for holding the eye 12 and an inserter 100 for introducing an intraocular shunt into the eye.

Embodiments of an intraocular shunt inserter are described herein. The shunt inserter can include a needle defining a lumen, A plunger can be partially disposed within the lumen of the needle. The plunger can advance a shunt through the needle to introduce the intraocular shunt into the eye.

A component driver can include an actuation member to move the plunger and/or the needle to prepare the inserter for ab externo or ab interno procedures. In some embodiments, the component driver can be actuated to change the position of the shunt relative to the bevel of the needle. The component driver can be coupled to, part of, or control a movement or position of a plunger or needle of the inserter.

For example, optionally, the component driver can be elongated or foreshortened from a first length to a second length to change the longitudinal relative position of the distal end portion of the plunger.

Further optionally, the component driver can be elongated or foreshortened from a first length to a second length to change the longitudinal relative position of the distal end portion of the needle.

Optionally, the inserter can include two component drivers, one component driver coupled to, part of, or control a movement or position of the plunger and another component driver coupled to, part of, or control a movement or position of the needle of the inserter.

In some embodiments, the component driver can be coupled to the needle to change the relative position of the distal end portion of the needle. In some embodiments, the component driver can be coupled to the plunger to change the relative position of the distal end portion of the plunger.

Figure 2:
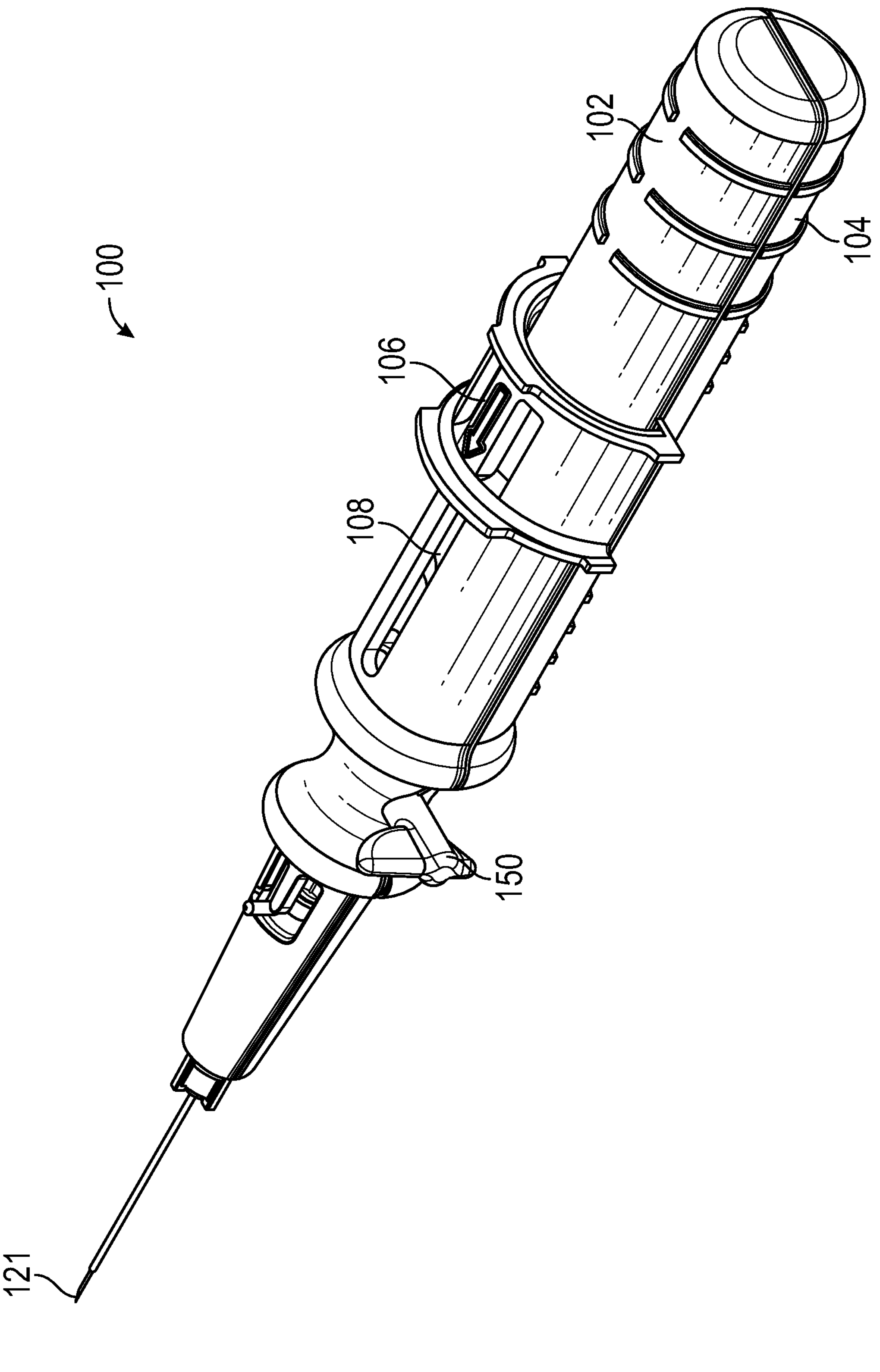
FIG. 2 is a perspective view of an inserter for implanting an intraocular shunt into an eye, according to some embodiments.

FIGS. 2-13 illustrate further details of the inserter 100 shown in FIG. 1. The inserter 100 can be actuated using a single hand, thus facilitating use of the inserter by an operator. The inserter 100 can comprise an upper housing 102, a lower housing 104, a slider component 106, and a needle 121. As shown in FIG. 2, the inserter 100 can be configured such that the slider component 106 is slidable along an elongate slot 108 of the housing 102. The slider component 106 can be selectively movable by an operator in order to actuate movement of components of the inserter 100.

For example, when the slider component 106 moves distally along the slot 108 (i.e., in a direction toward the needle 121), the slider component 106 can result in or cause a shunt (not shown) to be advanced within the needle 121, and in some embodiments, released from the needle 121. In accordance with some embodiments discussed further herein, movement of the slider component 106 can result in translational and/or rotational movement of components of the inserter 100. The sliding movement of the slider component 106 can be converted into rotational movement, which can thereafter be converted to movement along a longitudinal axis of the inserter 100. One of the benefits of this innovative and complex movement-conversion mechanism is that it enables embodiments of the inserter to provide precise, measured movements of its components within a compact assembly.

In the depicted example, the inserter 100 can be configured for ab externo procedures or ab interno procedures by rotating the removable key 150 prior to an implantation procedure. As described herein, the removable key 150 can be positioned in a vertical position (as shown in FIG. 2) to position the shunt relative to the needle 121 for ab externo procedures. Similarly, the removable key 150 can be rotated or otherwise positioned in a horizontal position to move the shunt relative to the needle 121 for ab interno procedures.

After configuring the inserter 100 for the ab externo procedure or the ab interno procedure, the removable key 150 can be removed or otherwise separated from the inserter 100. In some embodiments, the removable key 150 functions as an interlock to prevent the actuation of the inserter 100 until the removable key 150 is removed. Optionally, the removable key 150 can prevent the slider 106 from advancing until the removable key 150 is removed from the inserter 100.

Figure 3:
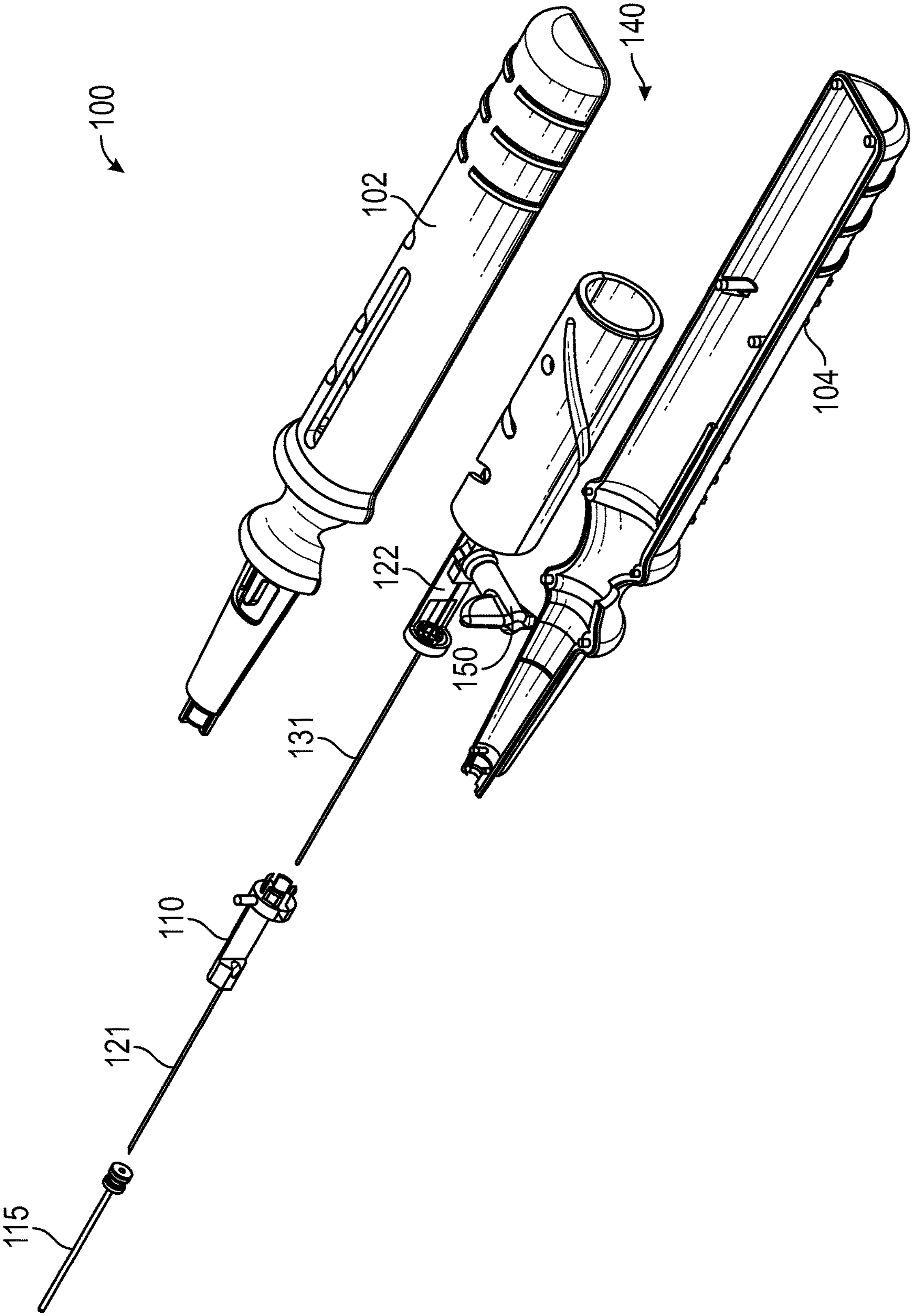
FIG. 3 is a perspective, exploded view of the inserter shown in FIG. 2, according to some embodiments.

As illustrated in FIG. 3, a plunger 131 can be disposed within the needle 121 to advance the shunt for implantation. The needle 121 can comprise a 25 GA or 27 GA needle. The plunger 131 can be slidably movable within a lumen of the needle 121 along a longitudinal axis of the inserter 100. Further, the needle 121 can be slidably movable within a lumen of the sleeve component 115 along the longitudinal axis. In some embodiments, the needle 121 can be attached to a movable needle base 110.

Each of the needle 121 and the plunger 131 can be coupled to respective drive components of a drive assembly 140 disposed within the housing 102 and 104. When in the assembled state, the inserter 100 can be configured such that the needle 121, the plunger 131, and the sleeve component 115 are aligned along or coaxial with the longitudinal axis. Some drive assemblies for actuating a plunger and for withdrawing a needle of an inserter are disclosed in U.S. patent application Ser. Nos. 13/336,803, 12/946,645, 12/620,564, 12/946,653, 12/946,565, and 11/771,805 and U.S. Pat. No. 9,585,790, the entireties of which are incorporated herein by reference.

Figure 4:
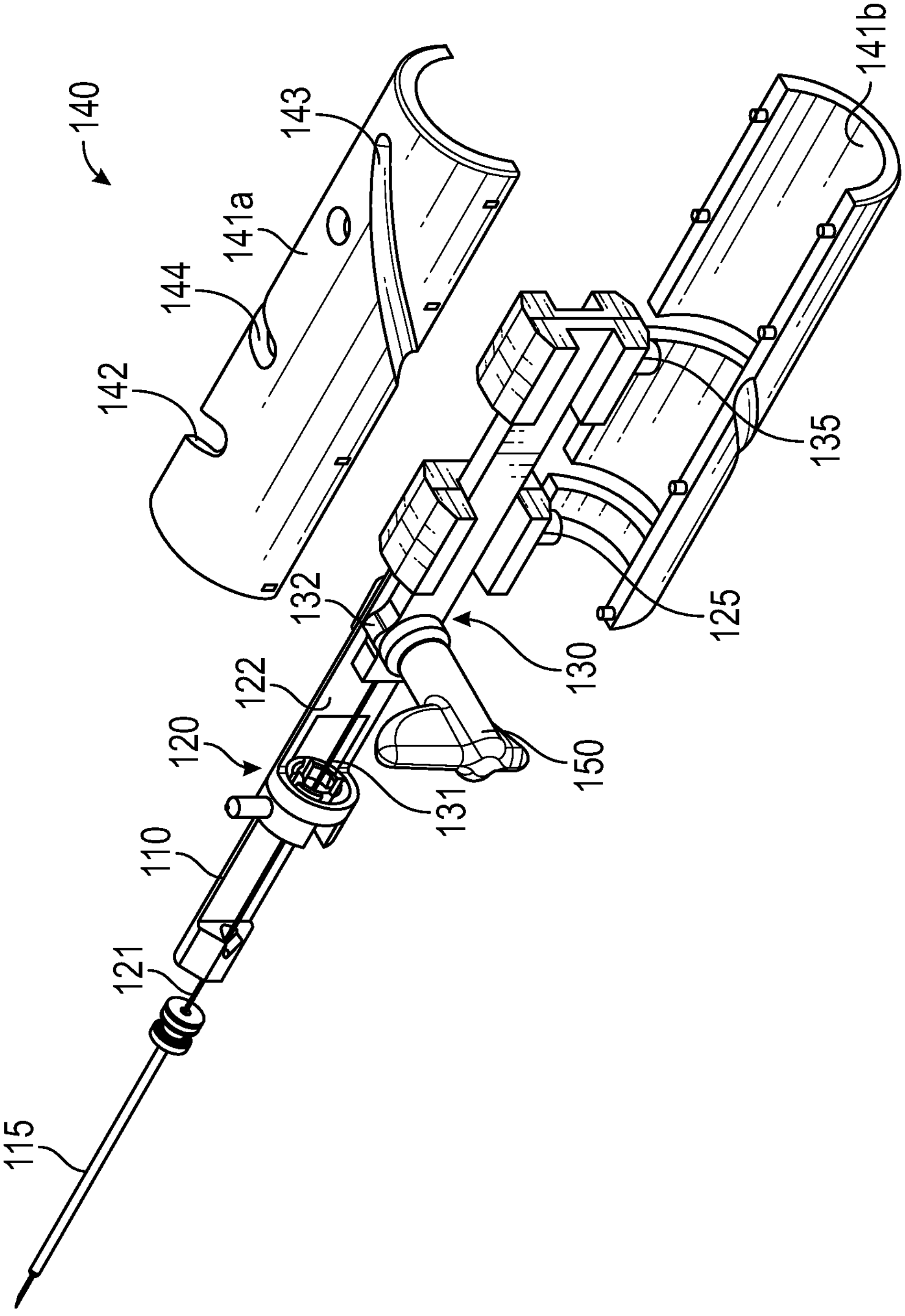
FIG. 4 is a perspective, exploded view of a drive assembly of the inserter shown in FIG. 2, according to some embodiments.

Referring to FIGS. 3 and 4, the needle 121, the plunger 131, and the sleeve 115 can be operably coupled to the drive assembly 140 and/or the housing 102. For example, a needle assembly 120 can operably couple the needle 121 to the drive assembly 140. The needle assembly 120 can include the needle 121, a needle base 110 and a needle driver 122. In the depicted example, the needle 121 can be coupled to the needle base 110. The needle base 110 can be fixedly coupled to a proximal end portion of the needle 121 such that rotational and longitudinal movement between the needle 121 and the needle base 110 is restricted or prevented. The needle base 110 can be enclosed within a distal end portion of the housing 102 when the inserter 100 is assembled. Further, as illustrated in FIG. 4 and discussed further below, the needle base 110 can be coupled to the drive assembly 140 via the needle driver 122.

Further, as shown in FIG. 4, a plunger assembly 130 can operably couple the plunger 131 to the drive assembly 140. The plunger assembly 130 can include the plunger 131 and a plunger driver 132. The plunger driver 132, can be fixedly coupled to a proximal end portion or midsection of the plunger 131 to restrict or prevent rotational and longitudinal movement of the plunger 131 relative to the plunger driver 132. Further, as illustrated in FIG. 4 and discussed further below, the plunger driver 132 can be coupled to the drive assembly 140.

Furthermore, the sleeve component 115 can be coupled to a portion of the housing 102 and 104. The sleeve 115 can be coupled so as to prevent rotational and longitudinal movement between the sleeve component 115 and the housing 102 and 104.

As noted above, the needle 121 and the plunger 131 can be operably coupled to the drive assembly 140. Such coupling can occur via the needle driver 122 and the plunger driver 132. In turn, the needle driver 122 and the plunger driver 132 can be coupled to one or more drive components that engage with the drive assembly 140 to the housing 102.

In accordance with some embodiments, the drive assembly 140 can be coupled to the needle 121 and the plunger 131 to actuate movement along the longitudinal axis of the needle 121 and the plunger 131 relative to the housing 102 and 104. For example, the drive assembly 140 can be configured to rotate or slide within the housing 102. The drive assembly 140 can transfer a longitudinal or axial force along the longitudinal axis to the needle component 121 and/or the plunger 131, independently or at the same time, to result in movement of the needle 121 and the plunger 131 relative to the housing 102 and 104 along the longitudinal axis.

As discussed herein, motion of the slider component 106 can result in motion of the drive assembly 140 and thereby result in motion of components of the drive assembly 140 relative to the housing 102 and 104. Some embodiments can be configured such that the slider component 106 can be longitudinally movable or slidable along the longitudinal axis relative to the housing 102 and 104 in order to drive or result in linear motion of the needle 121 and the plunger 131 and consequently a shunt.

As shown in FIG. 4, the drive assembly 140 can comprise drive components 141*a* and 141*b* configured to engage with the needle driver 122 and plunger driver 132. In some embodiments, longitudinal or linear motion of the slider component 106 along the longitudinal axis can be converted to result in rotation of the drive components 141*a* and 141*b* of the drive assembly 140, which can then be converted to result in longitudinal or linear motion of the needle 121 and the plunger 131 along the longitudinal axis relative to the housing 102 and 104. In accordance with some embodiments, motion of the components along the longitudinal axis can be parallel relative to the longitudinal axis.

FIG. 4 also illustrates an embodiment of the drive components 141*a* and 141*b*. The drive components 141*a* and 141*b* can comprise a groove 143 that can be configured to engage with a corresponding protrusion (not shown) of the slider component 106. Further, the drive components 141*a* and 141*b* can also comprise first and second driving grooves 142, 144 that can be configured to slidingly engage corresponding protrusions of the needle driver 122 and the plunger driver 132. Thus, the slider component 106 can comprise a protrusion, the needle driver 122 can comprise a protrusion 125, and the plunger driver 132 can comprise a protrusion 135. This arrangement of slots and protrusions can facilitate the transfer of motion from the slider component 106 to the respective ones of the needle 121 and the plunger 131. Further, the plunger driver 132 and the needle driver 122 can comprise rounded bodies that contact and slide against an inner guide surface of the drive components 141*a* and 141*b* when seated within the drive components 141*a* and 141*b*.

Figure 5:
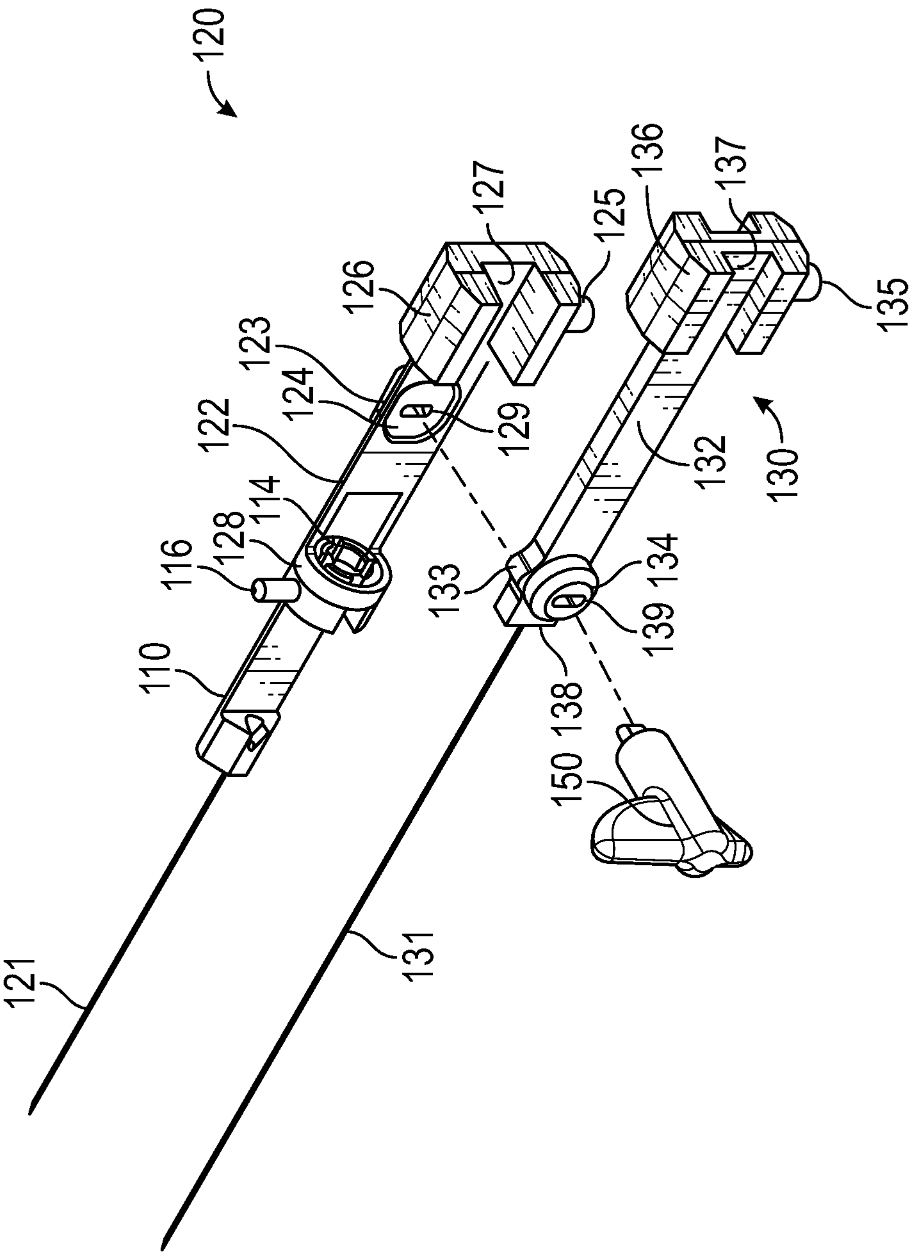
FIG. 5 is a perspective, exploded view of the needle assembly and the plunger assembly shown in FIG. 4, according to some embodiments.

As described herein, clinicians may select an ab externo approach or an ab interno approach to implant the shunt using the inserter 100 depending on the patient's needs and other factors. With reference to FIG. 5, the inserter 100 can be configured to position the shunt within the needle 121 for an ab externo approach or for an ab interno approach. As illustrated, the needle assembly 120 and/or the plunger assembly 130 can be configured to adjust the position of the shunt to be suitable for an ab externo approach or for an ab interno approach prior to the implantation procedure.

In some embodiments, portions of the needle assembly 120 and/or the plunger assembly 130 can be elongated, foreshortened, or otherwise changed to adjust the relative position of the needle 121 and/or the plunger 131 and consequently the relative position of the shunt for either ab externo or ab interno approaches. In the depicted example, the needle driver 122 and/or the plunger driver 132 can be elongated, foreshortened, or otherwise changed to adjust the position of the shunt.

For example, as shown in FIG. 5 the plunger driver 132 can be positioned in a foreshortened position and the needle driver 122 can be positioned in an elongated position for an ab externo approach. In some embodiments, the plunger driver 132 can be foreshortened by about 0.25 mm relative to an elongated configuration. Optionally, the plunger driver 132 can be foreshortened by about 0.05 mm, about 0.10 mm, about 0.15 mm, about 0.20 mm, about 0.30 mm, about 0.40 mm, or about 0.50 mm. In some embodiments, the needle driver 122 can be elongated approximately 1 millimeter relative to a foreshortened configuration. Optionally, the needle driver 122 can be elongated approximately about 0.8 mm, about 0.9 mm, about 1.1 mm, about 1.2 mm, about 1.3 mm, or about 1.5 mm. By foreshortening the plunger driver 132 and elongating the needle driver 122, the shunt can repositioned proximally relative to the bevel of the needle 121. In the ab externo configuration, the tip of the plunger 131 and therefore the shunt can be positioned approximately 7 mm from the bevel of the needle 121. Optionally, the tip of the plunger 131 can be positioned by about 4 mm, about 5 mm, about 6 mm, about 8 mm, about 9 mm, about 10 mm, or about 11 mm from the bevel of the needle 121 prior to actuation of the inserter 100. Upon actuation of the inserter 100, the plunger 131 can be advanced about 6 mm relative to the needle 121. In some embodiments, upon actuation of the inserter 100, the plunger 131 can be advanced by about 4 mm, about 5 mm, about 6 mm, about 8 mm, about 9 mm, about 10 mm, or about 11 mm relative to the needle 121.

Figure 6:
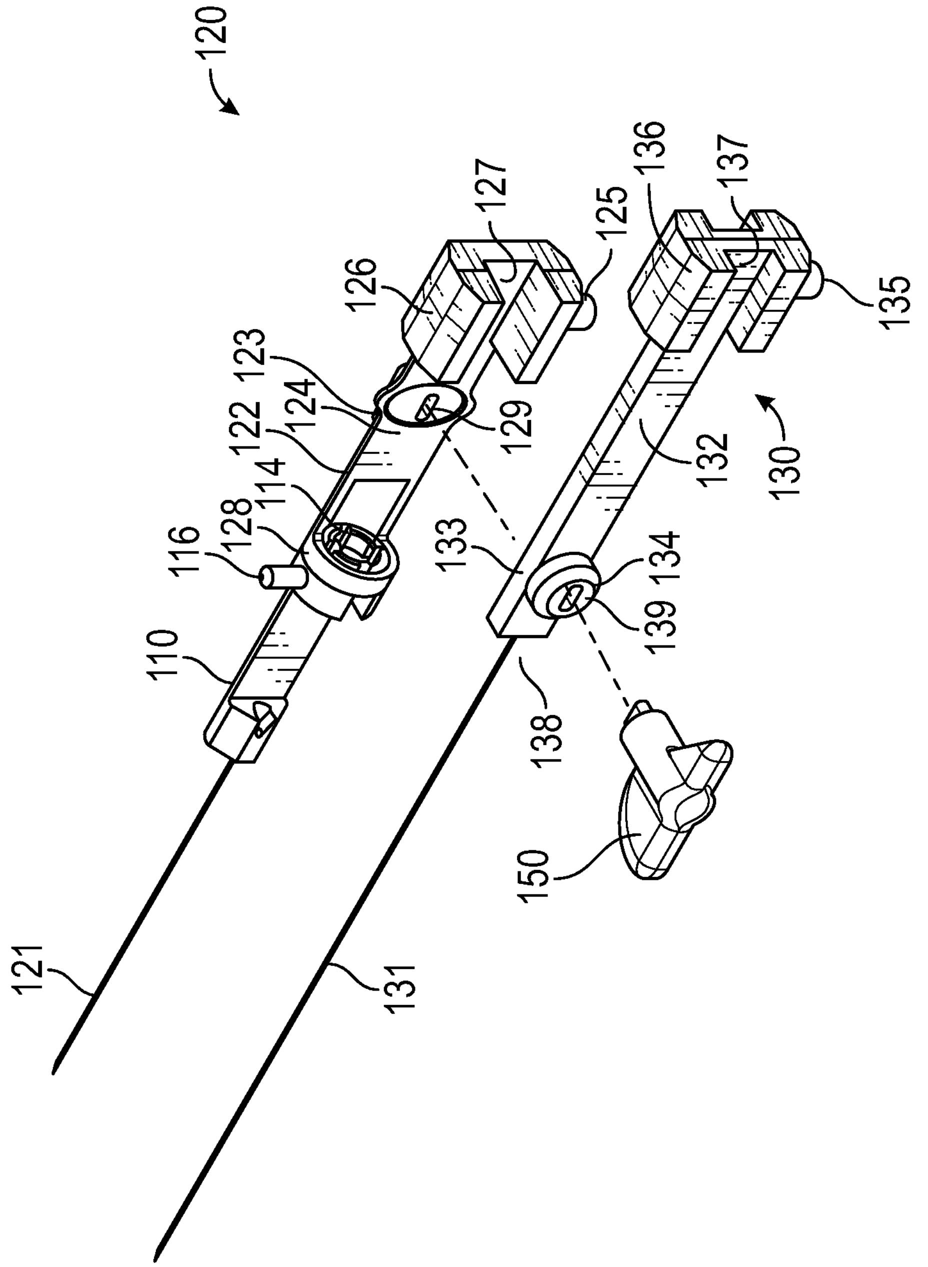
FIG. 6 is a perspective, exploded view of the needle assembly and the plunger assembly shown in FIG. 5 in an actuated position, according to some embodiments.

As shown in FIG. 6, the removable key 150 can be actuated to move the plunger driver 132 to an elongated position and the needle driver 122 to a foreshortened position for an ab interno approach. In some embodiments, the plunger driver 132 can be elongated by about 0.25 mm relative to an foreshortened configuration. Optionally, the plunger driver 132 can be elongated by about 0.05 mm, about 0.10 mm, about 0.15 mm, about 0.20 mm, about 0.30 mm, about 0.40 mm, or about 0.50 mm. In some embodiments, the needle driver 122 can be foreshortened approximately about 1 millimeter relative to an elongated configuration. Optionally, the needle driver 122 can be foreshortened by about 0.8 mm, about 0.9 mm, about 1.0 mm, about 1.1 mm, about 1.2 mm, about 1.3 mm, or about 1.5 mm. By elongating the plunger driver 132 and foreshortening the needle driver 122, the shunt can be positioned distally relative to the ab externo shunt position. In the ab interno configuration, the plunger 131 can extend and the needle 121 can retract to advance the shunt by about 1.25 mm relative to the needle 121 compared to the ab externo configuration. Therefore, in the ab interno configuration, the tip of the plunger 131 and therefore the shunt can be positioned about 5.75 mm from the bevel of the needle 121. Optionally, the tip of the plunger 131 can be positioned about 3 mm, about 4 mm, about 5 mm, about 5.5 mm, about 6 mm, about 7 mm, or about 8 mm from the bevel of the needle 121 prior to actuation of the inserter 100. Upon actuation of the inserter 100, the plunger 131 can be advanced approximately 6 mm relative to the needle 121. In some embodiments, upon actuation of the inserter 100, the plunger 131 can be advanced by about 4 mm, about 5 mm, about 6 mm, about 8 mm, about 9 mm, about 10 mm, or about 11 mm relative to the needle 121.

As can be appreciated, the inserter 100 can be provided with a default configuration that is suitable for ab externo or ab interno procedures. The removable key 150 can be used to change the configuration from an ab externo configuration to an ab interno configuration or vice versa.

Optionally, the removable key 150 can extend through portions of the needle driver 122 and/or the plunger driver 132 to prevent movement of the needle assembly 120 and/or the plunger assembly 130 relative to the housing 102 and 104, preventing inadvertent release of the shunt. Therefore, a clinician can utilize the removable key 150 to select the configuration of the inserter 100 and further prevent the release of the shunt until desired.

In some embodiments, the configuration of the inserter 100 can be changed by only altering the length of the needle assembly 120, only altering the length of the plunger assembly 130, or altering both the length of the needle assembly 120 and the length of the plunger assembly 130. In some embodiments the length of the needle driver 122 and the plunger driver 132 can be changed in opposing or different directions to change the configuration of the inserter 100.

Optionally, the length of the needle driver 122 and the plunger driver 132 can be changed simultaneously in a single action. In some embodiments, the nested arrangement of the needle driver 122 and the plunger driver 132 can allow the removable key 150 to engage with and actuate both the needle driver 122 and plunger driver 132 with a single action, simultaneously adjusting the length or configurations of the needle driver 122 and the plunger driver 132.

As can be appreciated, the needle driver 122 and/or the plunger driver 132 can utilize any suitable mechanism to elongate or foreshorten. As illustrated in FIGS. 5-11, the needle driver 122 and the plunger driver 132 can utilize cam mechanisms to adjust the length of the needle assembly 120 and/or the plunger assembly 130.

Figure 7:
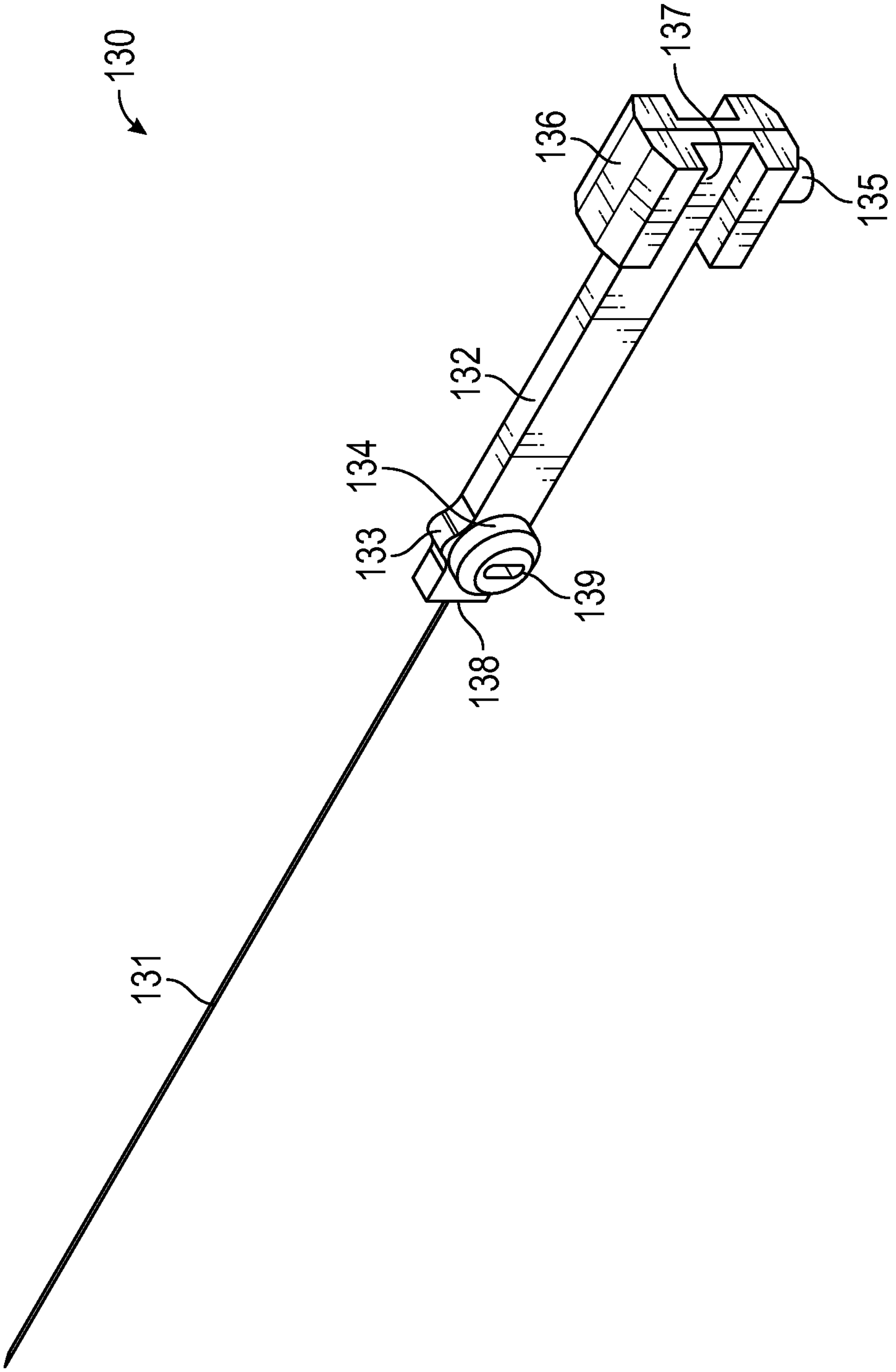
FIG. 7 is a perspective view of the plunger assembly shown in FIG. 4, according to some embodiments.

For example, the plunger assembly 130 allows for force or movement from the drive assembly 140 to actuate the plunger 131 and therefore the shunt. As shown in FIG. 7, the proximal end of the plunger 131 can be affixed or otherwise coupled to the distal end 138 of the plunger driver 132. As described herein, the drive assembly 140 can engage with and actuate the plunger driver 132 via the protrusion 135. The protrusion 135 can extend from the proximal end 137 of the plunger driver 132. Optionally, the rounded portion 136 can allow the plunger driver 132 to slide freely and be aligned within the drive assembly 140.

In the depicted example, a cam mechanism 134 can elongate or foreshorten the plunger driver 132. In some embodiments, the cam mechanism 134 can move the distal end 138 of the plunger driver 132 further or closer to the proximal end 137. In some embodiments, the cam mechanism 134 comprises a rotatable generally oblong shape with a major axis A and a minor axis B, such that the major axis A is longer than the minor axis B. As illustrated, the cam mechanism 134 can be rotated by the keyed slot 139. The removable key 150 can engage with the keyed slot 139 to actuate the cam mechanism 134. Optionally, the keyed slot 139 can be aligned with the major axis A of the cam mechanism 134.

Figure 8:
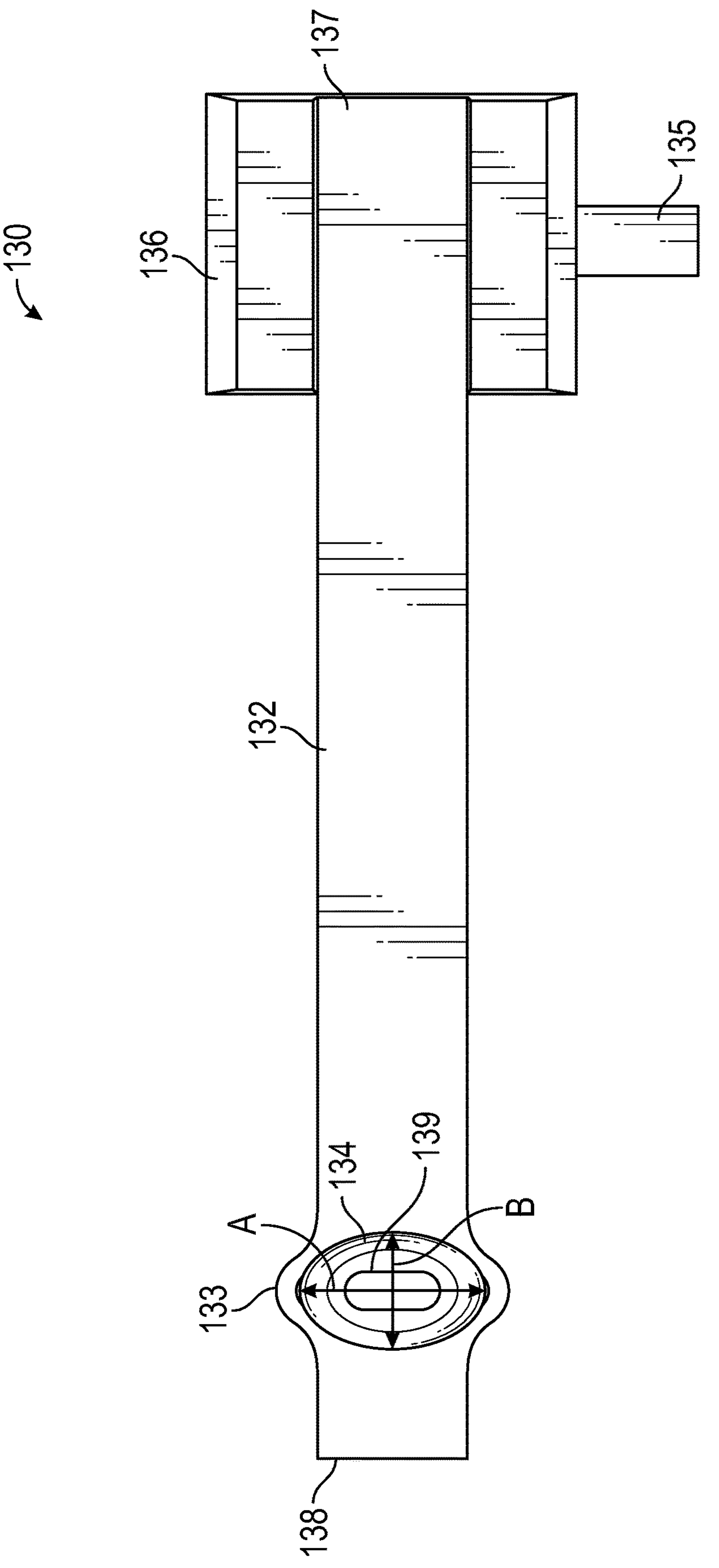
FIG. 8 is an elevation view of the plunger driver shown in FIG. 7, according to some embodiments.

As illustrated, the cam mechanism 134 can be disposed within an aperture 133. The aperture 133 can extend at least partially through the plunger driver 132. As described herein, the cam mechanism 134 can be actuated to positively displace the aperture 133, extending the plunger driver 132 or foreshortening the plunger driver 132. As illustrated in FIG. 8, the cam mechanism 134 can be rotated within the aperture 133 to align the major axis A of the cam mechanism 134 in a direction generally perpendicular to the length of the plunger driver 132, displacing the walls of the aperture 133 (e.g., creating a bulged portion) and foreshortening the plunger driver 132. In some embodiments, the foreshortened position of the plunger driver 132 corresponds with an ab externo treatment.

Figure 9:
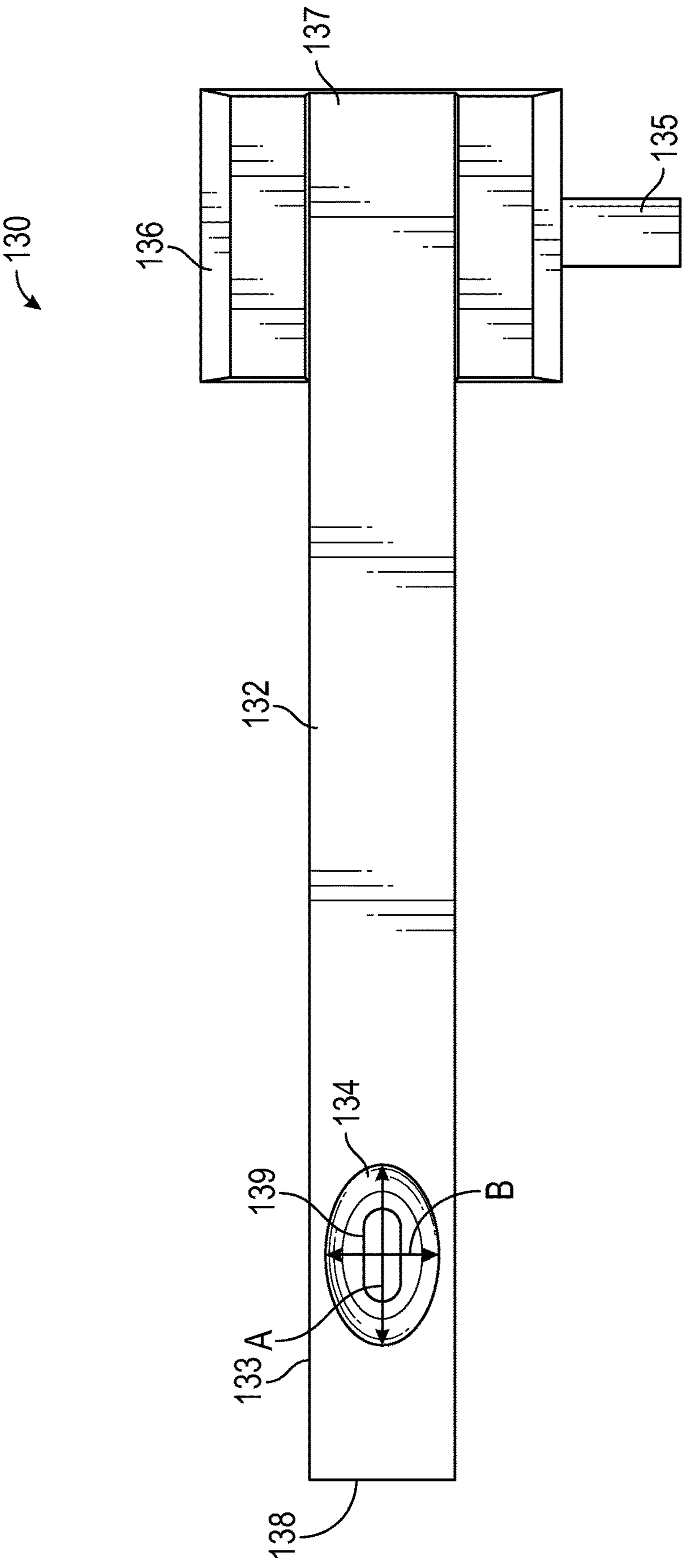
FIG. 9 is an elevation view of the plunger driver shown in FIG. 8 in an actuated position, according to some embodiments.

As illustrated in FIG. 9, the cam mechanism 134 can be rotated within the aperture 133 to align the major axis A of the cam mechanism 134 in a direction generally parallel to the length of the plunger driver 132, displacing the walls of the aperture 133 and elongating the plunger driver 132. In some embodiments, the elongated position of the plunger driver 132 corresponds with an ab interno treatment. In some embodiments, the rotation or actuation of the cam mechanism 134 does not elastically deform the plunger driver 132. In other words, the plunger driver 132 is may not be biased to return to any particular length without actuation.

Figure 10:
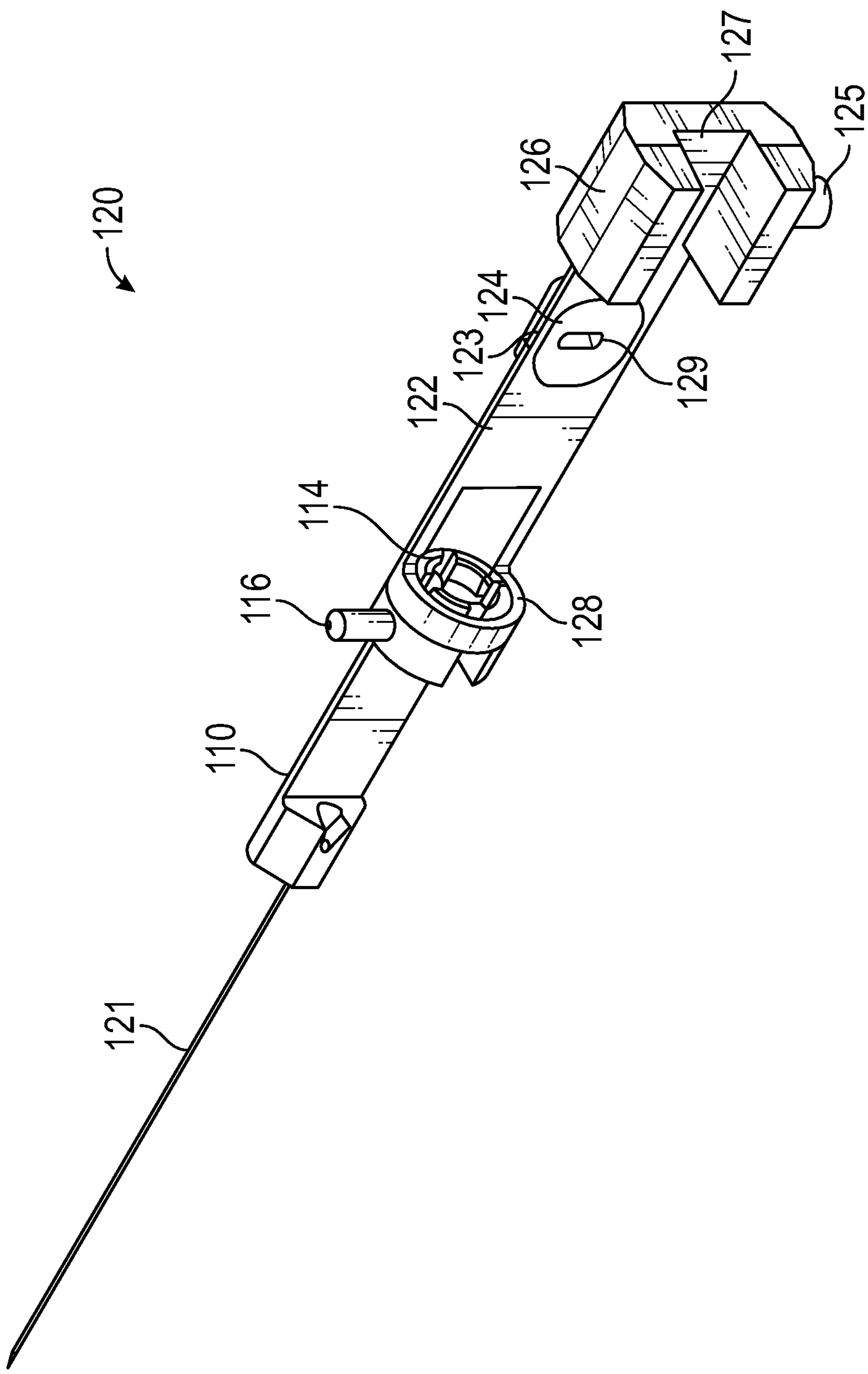
FIG. 10 is a perspective view of the needle assembly shown in FIG. 4, according to some embodiments.

Similarly, the needle assembly 120 allows for force or movement from the drive assembly 140 to actuate the needle 121. As shown in FIG. 10, the proximal end of the needle 121 can be affixed or otherwise coupled to the distal end 128 of the needle driver 122. Optionally, the proximal end of the needle 121 can be affixed to a needle base 110. The needle base 110 can be engaged with the distal end of the needle driver 122. The proximal end 114 of the needle base 110 can have a “snap” or friction fit with the distal end 128 of the needle driver 122. The needle driver 122 can have a complimentary or receiving aperture at the distal end 128. Optionally, the needle base 110 can include a rotational adjustment feature 116 to allow the clinician to adjust the rotation of the bevel of the needle 121.

As described herein, the drive assembly 140 can engage with and actuate the needle driver 122 via the protrusion 125. The protrusion 125 can extend from the proximal end 127 of the needle driver 122. Optionally, the rounded portion 126 can allow the needle driver 122 to slide freely and be aligned within the drive assembly 140.

In the depicted example, a cam mechanism 124 can elongate or foreshorten the needle driver 122 to adjust the position of the needle bevel relative to the distal end of the plunger 131, and therefore shunt. In some embodiments, the cam mechanism 124 can move the distal end 128 of the needle driver 122 further or closer to the proximal end 127. In some embodiments, the cam mechanism 124 comprises a rotatable generally oblong shape with a major axis C and a minor axis D, such that the major axis C is longer than the minor axis D. As illustrated, the cam mechanism 124 can be rotated by the keyed slot 129. The removable key 150 can engage with the keyed slot 129 to actuate the cam mechanism 124. In some embodiments, the keyed slot 129 can be aligned with the major axis C of the cam mechanism 124 (not pictured).

In some embodiments the keyed slot 129 of the needle assembly 120 can be aligned with the keyed slot 139 of the plunger assembly 130, allowing the removable key 150 to engage with both the needle assembly 120 and the plunger assembly 130. Advantageously, the plunger assembly 130 and the needle assembly 120 can be configured simultaneously with a single action or rotation of the removable key 150.

As illustrated in FIG. 5, the needle driver 122 can comprise a body having an aperture 123 extending therethrough. The cam mechanism 124 can be disposed through and rotatable within the aperture 123. As described herein, the cam mechanism 124 can be actuated to positively displace the aperture 123, extending the needle driver 122 or foreshortening the needle driver 122.

Figure 11:
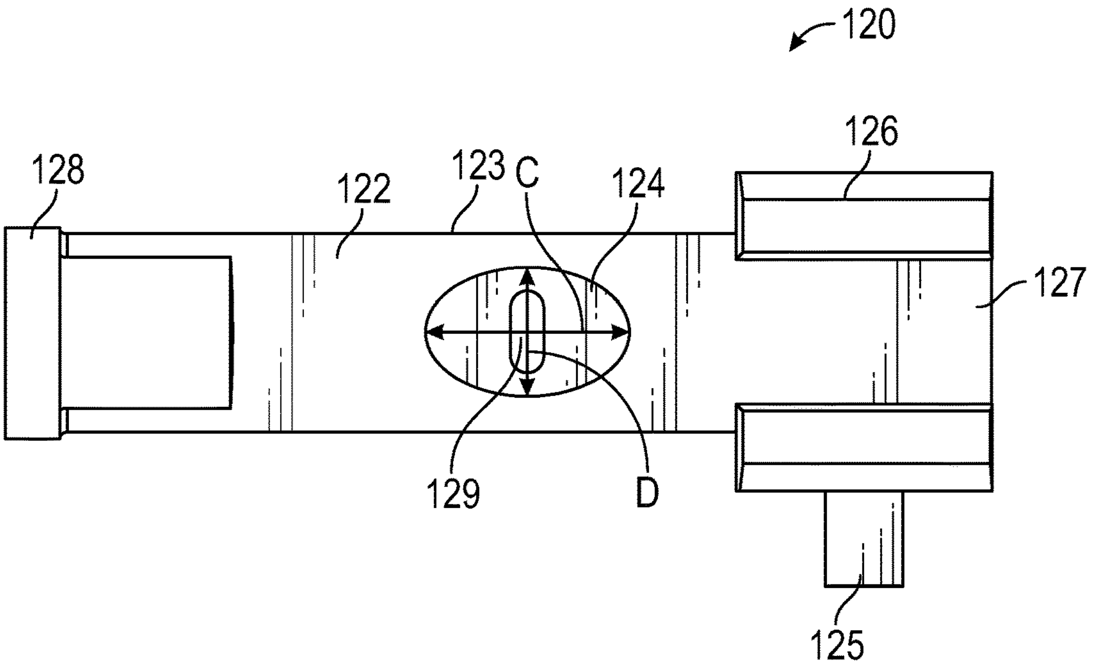
FIG. 11 is an elevation view of the needle driver shown in FIG. 10, according to some embodiments.

In some embodiments, as illustrated in FIG. 11, the cam mechanism 124 can be rotated within the aperture 123 to align the major axis C of the cam mechanism 124 in a direction generally parallel to the length of the needle driver 122, displacing the walls of the aperture 123 and elongating the needle driver 122. In some embodiments, the elongated position of the needle driver 122 corresponds with an ab externo treatment.

Figure 12:
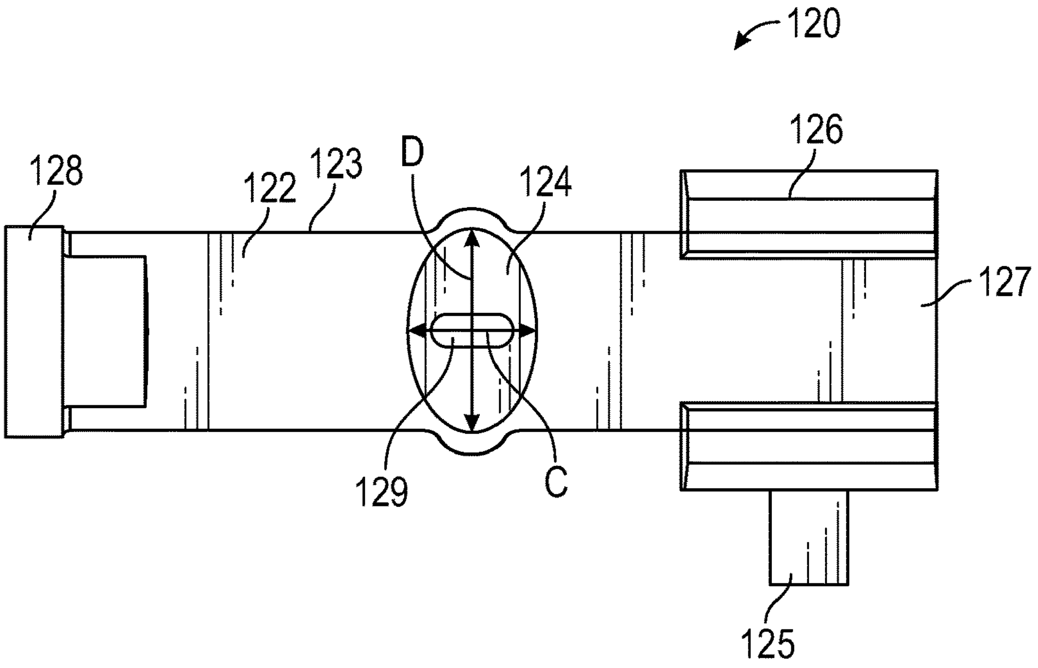
FIG. 12 is an elevation view of the needle driver shown in FIG. 11 in an actuated position, according to some embodiments.

As illustrated in FIG. 12, the cam mechanism 124 can be rotated within the aperture 123 to align the major axis C of the cam mechanism 124 in a direction generally perpendicular to the length of the needle driver 122, displacing the walls of the aperture (e.g., creating a bulged portion), thereby foreshortening the needle driver 122. In some embodiments, the foreshortened position of the needle driver 122 corresponds with an ab interno treatment.

In some embodiments, the rotation or actuation of the cam mechanism 124 does not elastically deform the needle driver 122. In other words, the needle driver 122 is may not be biased to return to any particular length without actuation.

Figure 13:
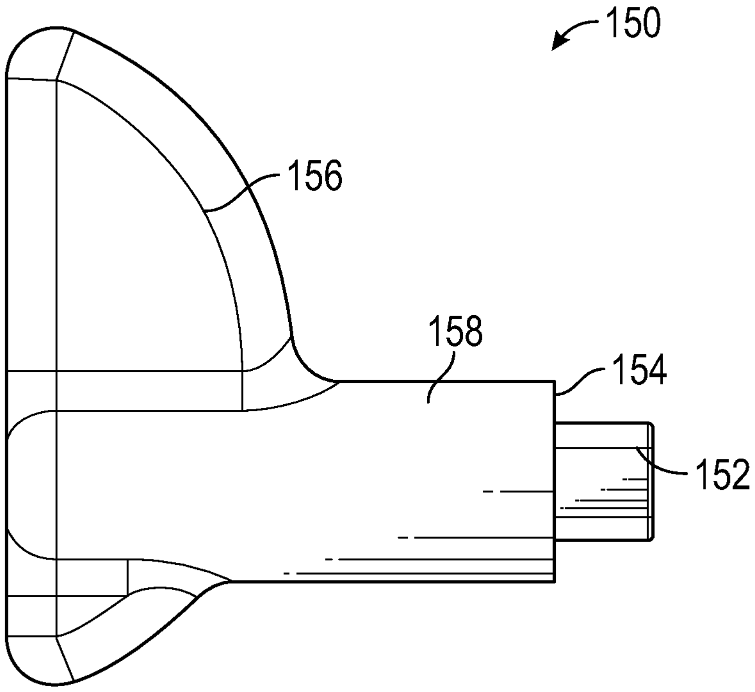
FIG. 13 is an elevation view of a rotatable key, according to some embodiments.

As illustrated in FIG. 13, the removable key 150 can be used to actuate the needle assembly 120 and/or the plunger assembly 130. In some embodiments, the removable key 150 is provided with the inserter 100. The removable key 150 includes an extension portion 152 that is configured to engage with the slot 129 and/or slot 139. The extension portion 152 can extend through both slots 129 and 139 to actuate both the needle assembly 120 and the plunger assembly 130 simultaneously. The body 158 of the removable key 150 can abut the housing 102 and 104. In some embodiments, the surface 154 can contact the housing 102 and 104. Optionally, a wing 156 can extend from the body 158 of the removable key 150, allowing a clinician to easily rotate the removable key 150.

As described herein, in addition to configuring the inserter 100 for ab externo and ab interno procedures, the removable key 150 can engage with the slots 129 and 139 to prevent the inadvertent actuation of the inserter 100. Optionally, the removable key 150 can engage with the needle assembly 120 and/or the plunger assembly 130 to prevent the drive assembly 140 from actuating the needle assembly 120 and/or the plunger assembly 130 relative to the housing 102 and 104. Upon removing the removable key 150 from the housing 102 and 104, the drive assembly 140 can actuate the needle assembly 120 and/or the plunger assembly 130.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

Illustration of Subject Technology as Clauses

Various examples of aspects of the disclosure are described below as clauses for convenience. These are provided as examples, and do not limit the subject technology.

Clause 1. An intraocular shunt inserter for treating glaucoma, comprising: a needle defining a lumen; and a plunger assembly comprising: a plunger at least partially disposed within the lumen of the needle, wherein the plunger is configured to advance a shunt through the lumen of the needle upon deployment; and a plunger driver coupled to a proximal end portion of the plunger, the plunger driver comprising an actuation member, wherein the plunger driver elongates from a first length to a second length upon movement of the actuation member for advancing a distal end portion of the plunger from a first position to a second position relative to the lumen.

Clause 2. The inserter of Clause 1, wherein the actuation member comprises an oblong cam, wherein the oblong cam is rotatable within the plunger driver about an axis oriented perpendicular relative to a longitudinal axis of the inserter.

Clause 3. The inserter of Clause 2, wherein the oblong cam comprises a major axis and a minor axis, and the plunger driver elongates from the first length to the second length by rotating the oblong cam to align the major axis with the longitudinal axis of the inserter.

Clause 4. The inserter of any one of the preceding Clauses, wherein the actuation member positively displaces the plunger driver from the first length to the second length.

Clause 5. The inserter of any one of the preceding Clauses, further comprising a removable key, wherein the removable key is releasably engaged with the actuation member to move the actuation member.

Clause 6. The inserter of Clause 5, wherein the removable key is releasably engageable with the actuation member.

Clause 7. The inserter of any one of the preceding Clauses, wherein the first position of the plunger corresponds to an ab externo treatment.

Clause 8. The inserter of any one of the preceding Clauses, wherein the second position of the plunger corresponds to an ab interno treatment.

Clause 9. An intraocular shunt inserter for treating glaucoma, comprising: a housing; a needle assembly comprising: a needle extending at least partially beyond a distal portion of the housing, the needle defining a lumen; and a needle driver coupled to a proximal end portion of the needle, the needle driver comprising an actuation member, wherein the needle driver foreshortens from a first length to a second length upon movement of the actuation member for retracting a distal end portion of the needle from a first position to a second position relative to the housing.

Clause 10. The inserter of Clause 9, wherein the actuation member comprises an oblong cam, wherein the oblong cam is rotatable within the needle driver about an axis oriented perpendicular relative to a longitudinal axis of the inserter.

Clause 11. The inserter of Clause 10, wherein the oblong cam comprises a major axis and a minor axis, and the needle driver retracts from the first length to the second length by rotating the oblong cam to align the minor axis with the longitudinal axis of the inserter.

Clause 12. The inserter of any one of Clauses 9 to 11, wherein the actuation member positively displaces the needle driver from the first length to the second length.

Clause 13. The inserter of any one of Clauses 9 to 12, further comprising a removable key, wherein the removable key is releasably engaged with the actuation member to move the actuation member.

Clause 14. The inserter of Clause 13, wherein the removable key is releasably engaged with the actuation member to prevent release of a shunt.

Clause 15. The inserter of any one of Clauses 9 to 14, wherein the first position of the needle corresponds to an ab externo treatment.

Clause 16. The inserter of any one of Clauses 9 to 15, wherein the second position of the needle corresponds to an ab interno treatment.

Clause 17. The inserter of any one of Clauses 9 to 16, further comprising a needle base coupled to the proximal end portion of the needle, wherein the needle base is coupled to the needle driver.

Clause 18. An intraocular shunt inserter for treating glaucoma, comprising: a housing; a needle assembly at least partially disposed within the housing and comprising a needle and a needle driver coupled to a proximal end portion of the needle; a plunger assembly at least partially disposed within the housing and comprising a plunger and a plunger driver coupled to a proximal end portion of the plunger, the plunger being at least partially disposed within a lumen of the needle, the plunger being configured to advance a shunt through the lumen of the needle; and an actuation mechanism being rotatable to change at least one of a length of the needle driver or a length of the plunger driver for permitting a clinician to adapt the inserter for a given surgical procedure.

Clause 19. The inserter of Clause 18, wherein the plunger driver moves in an opposing direction to the needle driver upon movement of the actuation mechanism.

Clause 20. The inserter of Clause 19, wherein the plunger driver extends and the needle driver retracts upon movement of the actuation mechanism.

Clause 21. The inserter of any one of Clauses 18 to 20, wherein the actuation mechanism positively displaces the needle driver from a first length to a second length.

Clause 22. The inserter of any one of Clauses 18 to 21, further comprising a needle base coupled to the proximal end portion of the needle, wherein the needle base is coupled to the needle driver.

Clause 23. The inserter of any one of Clauses 18 to 22, wherein the actuation mechanism positively displaces the plunger driver from a first length to a second length.

Clause 24. The inserter of any one of Clauses 18 to 23, further comprising a removable key, wherein the removable key is releasably engaged with actuation mechanism to simultaneously move the plunger driver and the needle driver.

Clause 25. The inserter of Clause 24, wherein the removable key is releasably engaged with the actuation mechanism.

Clause 26. The inserter of any one of Clauses 18 to 25, wherein the plunger driver is at least partially nested within the needle driver.

Clause 27. An intraocular shunt inserter for treating glaucoma, comprising: a needle defining a lumen and comprising a needle driver coupled to a proximal end portion of the needle; a plunger assembly comprising a plunger at least partially disposed within the lumen of the needle, wherein the plunger is configured to advance a shunt through the lumen of the needle upon release; and a component driver comprising an actuation member, wherein the component driver elongates from a first length to a second length upon movement of the actuation member for changing a longitudinal relative position of (i) a distal end portion of the plunger, when coupled to a proximal end portion of the plunger, or (ii) a distal end portion of the needle, when coupled to a proximal end portion of the needle.

Clause 28. The inserter of Clause 27, wherein the actuation member comprises an oblong cam, wherein the oblong cam is rotatable within a body of the component driver about an axis oriented perpendicular relative to a longitudinal axis of the inserter.

Clause 29. The inserter of Clause 28, wherein the oblong cam comprises a major axis and a minor axis, and the component driver elongates from the first length to the second length by rotating the oblong cam to align the major axis with the longitudinal axis of the inserter.

Clause 30. The inserter of any one of Clauses 27 to 29, further comprising a removable key, wherein the removable key is releasably engaged with the actuation member to move the actuation member.

Clause 31. The inserter of any one of Clauses 27 to 30, wherein the removable key is releasably engageable with the actuation member.

Clause 32. The inserter of any one of Clauses 27 to 31, further comprising a housing, the needle or the plunger being longitudinally movable from a first position to a second position relative to a distal portion of the housing.

Clause 33. The inserter of any one of Clauses 27 to 32, further comprising any of the features recited in Clauses 1 to 26.

Clause 34. The inserter of any one of Clauses 27 to 33, wherein the component driver is coupled to the proximal end portion of the needle.

Clause 35. The inserter of any one of Clauses 27 to 34, wherein the component driver is coupled to the proximal end portion of the plunger.

Clause 36. A method of operating an intraocular shunt inserter, the method comprising: partially disposing a plunger within a lumen of a needle; and moving a plunger driver actuation member to change a plunger driver from a first plunger driver length to a second plunger driver length, wherein the plunger driver is coupled to a proximal end portion of the plunger.

Clause 37. The method of Clause 36, further comprising moving a distal end portion of the plunger from a first plunger position to a second plunger position relative to the lumen prior to releasing a shunt through the lumen of the needle.

Clause 38. The method of any one of Clauses 36 to 37, further comprising moving a needle driver actuation member to change a needle driver from a first needle driver length to a second needle driver length, wherein the needle driver is coupled to the proximal end portion of the plunger.

Clause 39. The method of Clause 38, further comprising moving a distal end portion of the needle from a first needle position to a second needle position relative to the distal end portion of the plunger prior to releasing a shunt through the lumen of the needle.

Clause 40. The method of any one of Clauses 38 to 39, further comprising moving the plunger driver actuation member and the needle driver actuation member simultaneously.

Clause 41. The method of any one of Clauses 38 to 40, further comprising moving the plunger driver in an opposing direction to the needle driver upon movement of the plunger driver actuation member and the needle driver actuation member.

Clause 42. The method of any one of Clauses 38 to 41, further comprising extending the plunger driver upon movement of the plunger driver actuation member; and retracting the needle driver upon movement of the needle driver actuation member.

Clause 43. The method of any one of Clauses 38 to 42, wherein moving the needle driver actuation member further comprises rotating an oblong cam within the needle driver about an axis oriented perpendicular relative to a longitudinal axis of the inserter.

Clause 44. The method of Clause 43, further comprising rotating the oblong cam to align a minor axis with the longitudinal axis of the inserter.

Clause 45. The method of any one of Clauses 38 to 44, further comprising positively displacing the needle driver from the first length to the second length.

Clause 46. The method of any one of Clauses 38 to 45, further comprising releasably engaging the plunger driver actuation member and the needle driver actuation member with a removable key.

Clause 47. The method of Clause 46, further comprising preventing release of a shunt by engaging the plunger driver actuation member and the needle driver actuation member with the removable key.

Clause 48. The method of any one of Clauses 36 to 47, wherein moving the plunger driver actuation member further comprises rotating an oblong cam within the plunger driver about an axis oriented perpendicular relative to a longitudinal axis of the inserter.

Clause 49. The method of Clause 48, further comprising rotating the oblong cam to align a major axis with the longitudinal axis of the inserter.

Clause 50. The method of any one of Clauses 36 to 49, further comprising positively displacing the plunger driver from the first length to the second length.

Clause 51. A method of operating an intraocular shunt inserter that incorporates any of the steps or features recited in any of Clauses 1 to 50.

Clause 52. An intraocular shunt inserter comprising any of the features recited in any of Clauses 1 to 50.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. An intraocular shunt inserter for treating glaucoma, comprising:

a housing;

a needle assembly at least partially disposed within the housing and comprising a needle and a needle driver coupled to a proximal end portion of the needle;

a plunger assembly at least partially disposed within the housing and comprising a plunger and a plunger driver coupled to a proximal end portion of the plunger, the plunger being at least partially disposed within a lumen of the needle, the plunger being configured to advance a shunt through the lumen of the needle; and an actuation mechanism that is rotatable to change a length of at least one of the needle driver or the plunger driver to permit a clinician to adapt the inserter for a given surgical procedure, wherein rotation of the actuation mechanism displaces walls of an aperture defined in the needle driver or the plunger driver so as to change the length thereof.

2. The inserter of claim 1, wherein the plunger driver moves in an opposing direction to the needle driver upon movement of the actuation mechanism.

3. The inserter of claim 1, wherein the plunger driver extends and the needle driver retracts upon movement of the actuation mechanism.

4. The inserter of claim 1, wherein the actuation mechanism comprises an oblong cam, wherein the oblong cam is rotatable within a body of the needle driver about an axis oriented perpendicular relative to a longitudinal axis of the inserter.

5. The inserter of claim 1, wherein the actuation mechanism comprises an oblong cam, wherein the oblong cam is rotatable within a body of the plunger driver about an axis oriented perpendicular relative to a longitudinal axis of the inserter.

6. The inserter of claim 1, wherein the actuation mechanism comprises an oblong cam that comprises a major axis and a minor axis, and wherein the length of the needle driver and the length of the plunger driver changes by rotating the oblong cam to align the major axis with a longitudinal axis of the inserter.

7. The inserter of claim 1, further comprising a removable key, wherein the removable key is releasably engaged with the actuation mechanism to move the actuation mechanism.

8. The inserter of claim 1, wherein rotation of the actuation mechanism causes a portion of at least one of the needle driver or the plunger driver to deform so as to change a physical length of the needle driver or the plunger driver.

9. The inserter of claim 1, wherein the change in length comprises a lengthening of at least one of the needle driver or the plunger driver.

10. The inserter of claim 1, wherein the change in length comprises a foreshortening of at least one of the needle driver or the plunger driver.

11. An intraocular shunt inserter for treating glaucoma, comprising:

a needle defining a lumen and a proximal end portion of the needle;

a plunger assembly comprising a plunger at least partially disposed within the lumen of the needle, wherein the plunger is configured to advance a shunt through the lumen of the needle upon release; and a component driver comprising an actuation member and a body defining an aperture, wherein, upon displacement of walls of the aperture, the component driver elongates from a first length to a second length upon movement of the actuation member for changing a longitudinal relative position of at least one of a distal end portion of the plunger, when coupled to a proximal end portion of the plunger, or a distal end portion of the needle, when coupled to a proximal end portion of the needle.

12. The inserter of claim 11, wherein the actuation member comprises an oblong cam, wherein the oblong cam is rotatable within the body of the component driver about an axis oriented perpendicular relative to a longitudinal axis of the inserter.

13. The inserter of claim 12, wherein the oblong cam comprises a major axis and a minor axis, and the component driver elongates from the first length to the second length by rotating the oblong cam to align the major axis with the longitudinal axis of the inserter.

14. The inserter of claim 11, further comprising a removable key, wherein the removable key is releasably engaged with the actuation member to move the actuation member.

15. The inserter of claim 11, further comprising a housing, the needle or the plunger being longitudinally movable from a first position to a second position relative to a distal portion of the housing.

* * * * *